United States Patent [19]
Yabe et al.

[11] Patent Number: 5,688,221
[45] Date of Patent: Nov. 18, 1997

[54] ENDOSCOPE COVER FOR ENDOSCOPE SYSTEM HAVING UNIFORM FLEXIBILITY

[75] Inventors: Hisao Yabe, Hachioji; Yoshihiro Iida, Tama; Akira Suzuki, Hachioji; Hideo Ito, Hachioji; Yoshio Tashiro, Hino; Minoru Yamazaki, Hachioji; Osamu Tamada, Hachioji; Tatsuya Furukawa, Hachioji, all of Japan

[73] Assignee: Olympus Optical Co., Ltd., Tokyo, Japan

[21] Appl. No.: 37,282

[22] Filed: Mar. 26, 1993

[30] Foreign Application Priority Data

Feb. 12, 1993 [JP] Japan .................. 5-004271 U
Feb. 12, 1993 [JP] Japan .................. 5-024548

[51] Int. Cl.$^6$ ............................................. A61B 1/04
[52] U.S. Cl. .......................................... 600/121; 600/139
[58] Field of Search ..................... 128/4, 6; 600/121, 600/122, 123, 124, 125, 139, 140, 141

[56] References Cited

U.S. PATENT DOCUMENTS

| | | |
|---|---|---|
| Re. 34,110 | 9/1992 | Opie . |
| 3,162,190 | 12/1964 | Del Gizzo . |
| 4,646,722 | 3/1987 | Silverstein ................ 128/4 |
| 4,721,097 | 1/1988 | D'Amelio ................. 128/4 |
| 4,741,326 | 5/1988 | Sidall ...................... 128/4 |
| 4,825,850 | 5/1989 | Opie ........................ 128/4 |
| 4,869,238 | 9/1989 | Opie ........................ 128/6 |
| 4,886,049 | 12/1989 | Darras ..................... 128/4 |
| 4,907,395 | 3/1990 | Opie ........................ 53/434 |
| 4,991,564 | 2/1991 | Takahashi ................ 128/4 |
| 4,991,565 | 2/1991 | Takahashi ................ 128/4 |
| 4,997,084 | 3/1991 | Opie ........................ 206/364 |
| 5,050,585 | 9/1991 | Takahashi ................ 128/4 |
| 5,058,567 | 10/1991 | Takahashi ................ 128/4 |
| 5,201,908 | 4/1993 | Jones ....................... 128/4 |
| 5,217,001 | 6/1993 | Nakao et al. ............. 128/4 |
| 5,359,991 | 11/1994 | Takahashi et al. ....... 128/4 |

FOREIGN PATENT DOCUMENTS

| | | |
|---|---|---|
| 0 184 778 | 6/1986 | European Pat. Off. . |
| 0 310 515 | 4/1989 | European Pat. Off. . |
| 0 338 567 | 10/1989 | European Pat. Off. . |
| 0 341 718 | 11/1989 | European Pat. Off. . |
| 0 341 719 | 11/1989 | European Pat. Off. . |
| 0 349 479 | 1/1990 | European Pat. Off. . |
| 0 440 252 | 8/1991 | European Pat. Off. . |
| 0 440 254 | 8/1991 | European Pat. Off. . |
| 0 444 429 | 9/1991 | European Pat. Off. . |
| 39 09 290 | 10/1989 | Germany . |
| 51-47587 | 4/1976 | Japan . |
| 51-103891 | 8/1976 | Japan . |
| 52-95284 | 7/1977 | Japan . |
| 58-44033 | 3/1983 | Japan . |
| 62-177701 | 11/1987 | Japan . |
| 1-140902 | 9/1989 | Japan . |
| 2-57228 | 2/1990 | Japan . |
| 2-54734 | 11/1990 | Japan . |
| 3-13105 | 2/1991 | Japan . |
| 3-29634 | 2/1991 | Japan . |

(List continued on next page.)

*Primary Examiner*—Beverly M. Flanagan
*Attorney, Agent, or Firm*—Armstrong, Westerman, Hattori, McLeland & Naughton

[57] ABSTRACT

An endoscope cover according to the present invention has an arrangement that at least a portion of a control-portion cover for covering the control portion of a cover-type endoscope that corresponds to a soft portion of the cover-type endoscope has uniform flexibility that does not deteriorate the flexibility of said soft portion so that the insertion facility at the time of an inspection with the endoscope is maintained. An endoscope system of a type having an endoscope cover according to the present invention has a warp control knob disposed away from the body of a control portion also serving as a holding portion of the cover-type endoscope, the system having an arrangement that a warping mechanism included in the body of the control portion and the warp control knob are connected to each other by a connection member.

4 Claims, 31 Drawing Sheets

FOREIGN PATENT DOCUMENTS

| | | |
|---|---|---|
| 3-29635 | 2/1991 | Japan . |
| 3-37029 | 2/1991 | Japan . |
| 3-37030 | 2/1991 | Japan . |
| 3-221024 | 9/1991 | Japan . |
| 3-101901 | 10/1991 | Japan . |
| 3-101902 | 10/1991 | Japan . |
| 3-101903 | 10/1991 | Japan . |
| 3-101904 | 10/1991 | Japan . |
| 3-101905 | 10/1991 | Japan . |
| 3-101906 | 10/1991 | Japan . |
| 3-101907 | 10/1991 | Japan . |
| H4-325138 | 11/1992 | Japan . |

ENDOSCOPE COVER FOR ENDOSCOPE SYSTEM HAVING UNIFORM FLEXIBILITY

BACKGROUND OF THE INVENTION

1. Field of the Invention

The present invention relates to an endoscope cover for preventing contamination of an endoscope and to an endoscope system having the cover.

2. Description of the Related Art

Recently, endoscopes have been widely used in the medical field and so forth. A medical inspection performed with an endoscope must involve a clean endoscope that has previously been cleaned and disinfected. The time and cost required to clean and disinfect the endoscope have been factors which deteriorate the efficient use of the endoscope.

Accordingly, a technology has evolved involving the endoscope which has a cover for the endoscope whereby the endoscope can be protected from uncleanliness even after it has been used and the necessity of cleaning and sterilizing the endoscope can be eliminated. The endoscope cover system has been disclosed in, for example, Japanese Patent Publication No. 1990-54,734 and U.S. Pat. No. 3,162,190.

The foregoing endoscope cover system includes a clean cover, which has previously been subjected to a sterilization process, is used to cover the endoscope, and the cover is removed from the endoscope and disposed after an inspection has been completed. Therefore, the endoscope cover is used and disposed for each patient, resulting in satisfactory cleanliness. As a result, the labor required to clean and disinfect the endoscope can be eliminated.

It should be noted that the endoscope so arranged to be used with the foregoing endoscope cover fastened thereto has substantially the same structure as a conventional endoscope so arranged to be used without the cover. A conventional endoscope so arranged to be used without the cover can be used with the cover fastened thereto.

That is, the endoscope of the type having the cover comprises an elongated insertion portion and a large-diameter control portion disposed adjacently to the trailing portion of the insertion portion. The insertion portion is composed of a hard leading portion, a bending portion disposed adjacently to the trailing portion of the leading portion and capable of warping both vertically and laterally, and a flexible portion made of an elongated flexible tube disposed between the bending portion and the control portion. The flexible portion is, for example, formed so that the leading portion is more flexible in comparison to the portion adjacent to the operator, resulting in an improvement in the insertion facility into the body cavity at the time of the inspection using the endoscope.

However, the conventional cover for the endoscope must be adaptable to a variety of types of endoscopes including those in which the warping portions have different lengths, resulting in no particular consideration being made about the flexibility of the portion for covering the insertion portion of the endoscope arranged to be used with the cover. It leads to a fact that the flexibility of the insertion portion into the body cavity cannot be made uniform. In particular, an endoscope cover that is provided with channels, such as a channel for a curing tool and a channel for an air/water supply pipe, for the purpose of overcoming the difficulty in cleaning and disinfecting the endoscope, easily encounters the foregoing problem of the non-uniform flexibility of the insertion portion.

In the state where the endoscope is covered with the cover, the expected insertion facility into the body cavity deteriorates, resulting in worsening of the operation facility of the endoscope. What is worse, the insertion of the endoscope inflicts pain on a patient.

The foregoing endoscopes of a type for use with a cover are classified into an optical endoscope that enables a visual inspection through the ocular portion thereof and an electronic endoscope that incorporates a solid-state image sensing device, such as a charge-coupled-device (CCD), disposed in the image-sensing potion in the leading portion of the insertion portion thereof. The optical endoscope with the type for use with the cover is usually used with an external camera, such as a camera or a video camera, that is attached on the outer surface of the ocular portion of the endoscope in order to meet a need of recording the observed image or processing the image.

Since the conventional endoscope cover has, however, been arranged to have the size and to enable the operation facility of the endoscope to be obtained when it is used to cover only the endoscope, skill is demanded for fastening the external camera to the endoscope behind, for example, a sheet-like flexible endoscope cover. Even if the camera can be fastened, the external camera is not covered with the endoscope cover and, accordingly, it is contaminated. It takes a great amount of labor and a long time to clean and disinfect the contaminated external camera. Moreover, the external camera is too expensive to dispose the contaminated external camera at each endoscope inspection.

SUMMARY OF THE INVENTION

An object of the present invention is to provide an endoscope cover and an endoscope system of a type having a cover for covering the endoscope that enable satisfactory operation facility in operating the endoscope while maintaining insertion facility of an insertion portion of the endoscope into a subject to be inspected.

Another object of the present invention is to provide an endoscope cover and an endoscope system of a type having a cover for covering the endoscope having an arrangement in which the endoscope is covered with the endoscope cover to prevent contamination while also preventing contamination of an external camera attached to an ocular portion of the endoscope.

An endoscope cover according to the present invention comprises an insertion-portion cover for covering an insertion portion of a cover-type endoscope and a control-portion cover connected to the insertion portion cover and covering a control portion of the cover-type endoscope, wherein at least a portion of the insertion-portion cover corresponding to a flexible portion of the cover-type endoscope has uniform flexibility that does not deteriorate the flexibility of the soft portion.

An endoscope system of a type having a cover for covering an endoscope according to the present invention comprises a body of a control portion also serving as a holding portion; a bending mechanism included in the body of the control portion; a bending control knob disposed away from the body of the control portion; and a connection member for establishing a connection between the bending control knob and the bending mechanism.

Other and further objects, features and advantages of the invention will be appear more fully from the following description.

BRIEF DESCRIPTION OF THE DRAWINGS

FIG. 1 is a cross sectional view which illustrates a cover leading portion;

FIG. 2 is a cross sectional view which illustrates a portion including a bending control knob;

FIG. 3 illustrates a cover holder;

FIG. 4 illustrates the relationship between a cover holding member and a control-portion fixing joint portion;

FIG. 5 is an overall view which illustrates the structure of an endoscope apparatus of a channel-provided endoscope cover type;

FIG. 6 is a cross sectional view which illustrates the schematic structure of the channel-provided endoscope cover;

FIG. 7 is a cross sectional view which illustrates an insertion-portion cover;

FIG. 8 is a perspective view which illustrates a cover leading portion;

FIG. 9 is a front elevational view which illustrates the cover leading portion;

FIG. 10 is a cross sectional view which illustrates the schematic structure of the channel-provided endoscope cover;

FIG. 11 is a cross sectional view which illustrates the schematic structure of the channel-provided endoscope cover;

FIG. 12 is an overall view which illustrates the structure of an endoscope apparatus of the endoscope cover type;

FIG. 13 illustrates the shape of the channel-provided endoscope cover;

FIG. 14 is a cross sectional view which illustrates an insertion-portion cover;

FIG. 15 is a perspective view which illustrates the cover leading portion;

FIG. 16 is a front elevational view which illustrates the cover leading portion;

FIG. 17 is a front elevational view which illustrates a cover member corresponding to a portion opposing the warp control knob;

FIG. 18 is a front elevational view which illustrates a cover member corresponding to the bending control knob;

FIG. 19 illustrates a state where a fastener portion is opened;

FIG. 20 illustrates a state where the fastener portion is closed;

FIG. 21 is a side elevational view which illustrates a state where a control portion of the cover-type endoscope and a video camera are covered with a control-portion cover;

FIG. 22 is a top view which illustrates a state where the control portion of the cover-type endoscope and the video camera are covered with the control-portion cover;

FIG. 23 illustrates a state where another fastener portion is opened;

FIG. 24 illustrates a state where the other fastener portion is closed;

FIG. 25 illustrates the shape of the channel-provided endoscope cover;

FIG. 26 illustrates the control-portion cover in a state where the fastener portion is opened;

FIG. 27 illustrates the shape of the channel-provided endoscope cover;

FIG. 28 is a front elevational view which illustrates the cover member corresponding to a portion opposing the bending control knob;

FIG. 29 is a front elevational view which illustrates the cover member corresponding to the warp control knob;

FIG. 30 is a side elevational view which illustrates a state where the control portion of the cover-type endoscope and the camera are covered with the control-portion cover;

FIG. 31 is a top view which illustrates a state where the control portion of the cover-type endoscope and the camera are covered with the control-portion cover;

FIG. 32 illustrates the shape of the channel-provided endoscope cover;

FIG. 33 illustrates the control-portion cover in a state where the fastener portion is opened;

FIG. 34 illustrates the trailing end of the control-portion cover;

FIG. 35 illustrates the shape of the channel-provided endoscope cover;

FIG. 36 is radial-directional cross sectional view which illustrates the insertion-portion cover;

FIG. 37 is a radial-directional cross sectional view which illustrates a control-portion fixing joint portion;

FIG. 38 illustrates the control-portion cover;

FIG. 39 is a front elevational view which illustrates the cover body;

FIG. 40 illustrates a fastening portion of the control-portion cover to fasten the endoscope control portion fixing joint portion;

FIG. 41 illustrates the connection between the endoscope control portion fixing joint portion and the control-portion cover;

FIG. 42 illustrates the control-portion cover to which the cover-type endoscope is fastened;

FIG. 43 illustrates a universal cord cover;

FIG. 44 illustrates the connection between the universal cord cover and the control-portion cover;

FIG. 45 is a cross sectional view which illustrates a portion including the warp control knob;

FIG. 46 is a cross sectional view which illustrates a control-portion fixing joint portion of a two-directional scope cover;

FIG. 47 is a cross sectional view which illustrates a control-portion fixing joint portion of a four-directional scope cover;

FIG. 48 illustrates the position of the bending control knob with respect to the control-portion of the endoscope;

FIG. 49 is a cross sectional view which illustrates a portion including the bending control knob and a warp control shaft;

FIG. 50 illustrates the position of the bending control knob and an engagement knob with respect to the control portion of the endoscope;

FIG. 51 is a perspective view which illustrates a holding member of a cover holder;

FIG. 52 illustrates the holding member;

FIG. 53 illustrates a state where the control-portion fixing joint portion is held by the holding member; and FIG. 54 illustrates a state where the control-portion fixing joint portion is held by the holding member.

DETAILED DESCRIPTION OF THE PREFERRED EMBODIMENTS

FIGS. 5 to 9 illustrate a first embodiment of the present invention.

Figure 5:
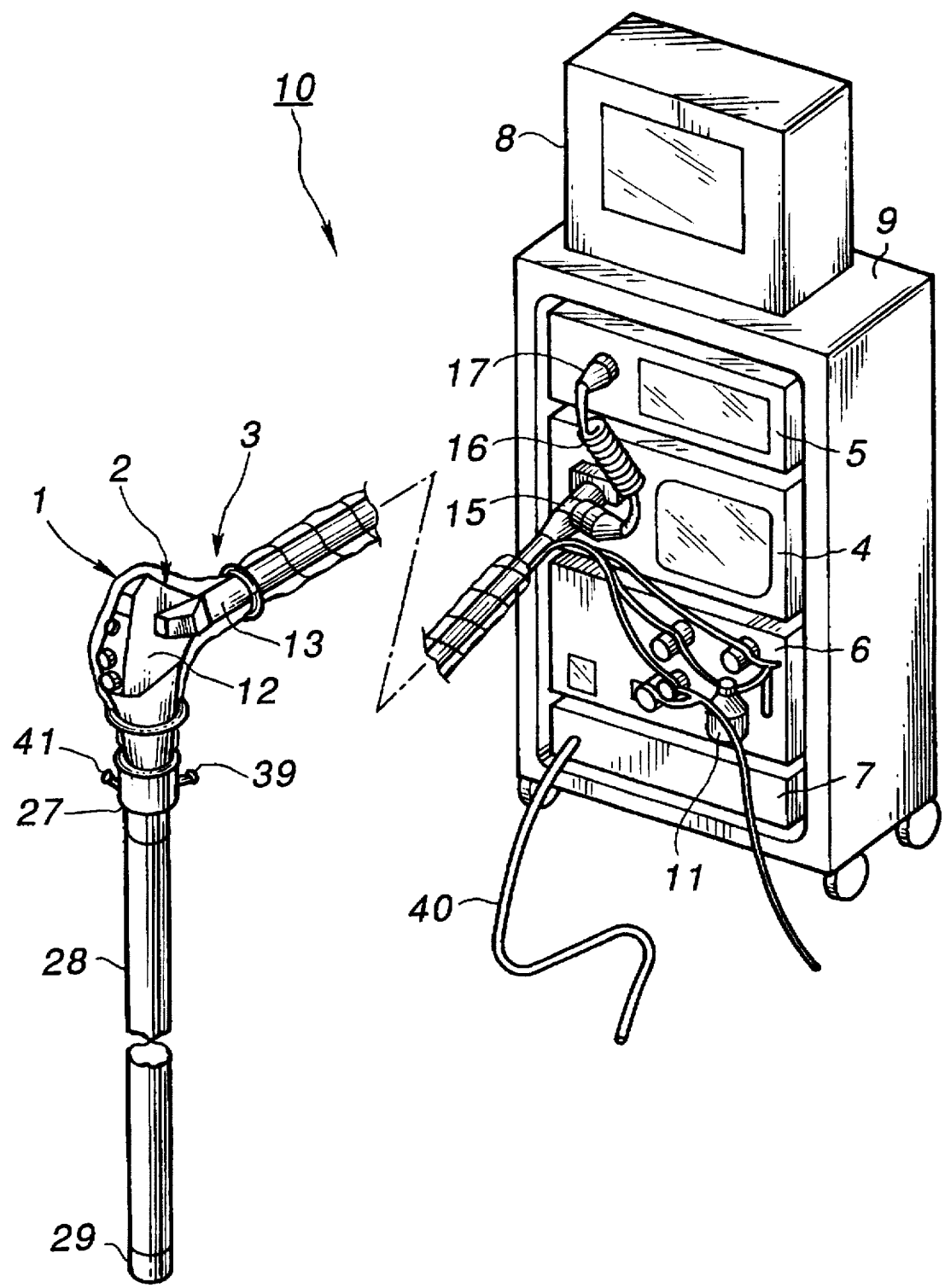
FIGS. 5 to 9 illustrate a first embodiment of the present invention.

Referring to FIG. 5, reference numeral 10 represents an endoscope apparatus comprising an endoscope-cover-type endoscope being used so that a cover-type endoscope 2 is covered with a channel-provided endoscope cover (hereinafter abbreviated to a "cover") 1.

A variety of peripheral devices, such as a light source device 4, a video processor 5, a fluid control device 6, an expander 7 (hereinafter abbreviated to an "expander") for a channel-provided endoscope cover, and a monitor 8, are connected to the cover-type endoscope 3. Furthermore, the monitor 8 is mounted on the ceiling plate of a cart 9 while causing the other peripheral devices to be accommodated in the cart 9.

The light source device 4 supplies irradiation light to the cover-type endoscope 2. The video processor 5 converts, into a standard video signal, an electric signal supplied from the cover-type endoscope 2, which is the electronic endoscope, to output the video signal to the monitor 8. The monitor 8 receives the video signal to display an endoscope image.

The fluid control apparatus 6 supplies air/water through a tubular passage disposed in the cover 1 and to be described later. Therefore, a water supply source 11 and an air supply source (omitted from illustration) are disposed in the fluid control device 6. The tubular passage connected to the water supply source 11 and the air supply source (omitted from illustration) is controlled by an electromagnetic valve so that they are opened/closed. The expander 7 supplies air to the cover 1 to expand the cover 1 so that the cover 1 can easily be fastened/removed to and from the cover-type endoscope 2.

The cover-type endoscope 2 is structured substantially similarly to a conventional endoscope for use without a cover, the cover-type endoscope 2 comprising a large-diameter control portion 12 having an air/water supply switch and a suction switch and the like, a universal cord extending from the side portion of the control portion 12 and an elongated insertion portion 14 (see FIG. 6) extending from the base portion of the control portion 12. The cover-type endoscope 2 is detachably connected to the light source device 4 via a connector 15 disposed in the trailing portion of the universal cord 13. The connector 15 is detachably connected to the video processor 5 via a signal connector 17 disposed at the trailing end of a cable 16 extending from the side portion of the connector 15.

Figure 6:
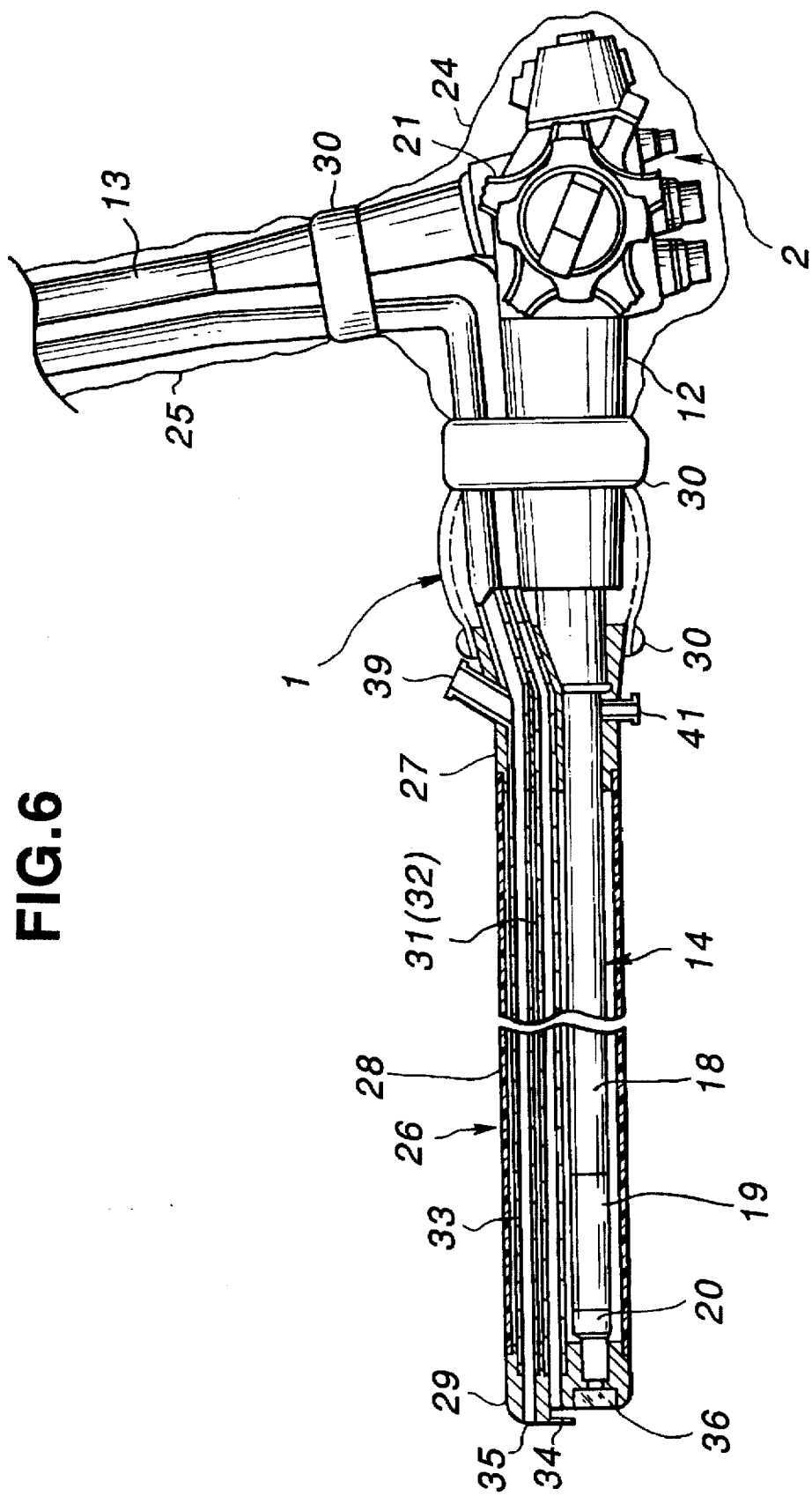

The insertion portion 14 of the cover-type endoscope 2 is, as shown in FIG. 6, composed of a flexible portion 18 made of a flexible tube, a bending portion 19 permitted to be bent, a hard leading portion 20 having a semicircular cross sectional shape and arranged to be fastened to a cover leading portion 29 of the cover 1 to be described later which are disposed in this sequential order when viewed from the base portion of the control portion 12 toward the leading portion. The flexible portion 18 is arranged so that, for example, its leading portion is more flexible than a portion adjacent to an operator, resulting in satisfactory insertion facility into the body cavity at the time of an endoscope inspection similarly to the conventional cover-less endoscope.

Figure 7:
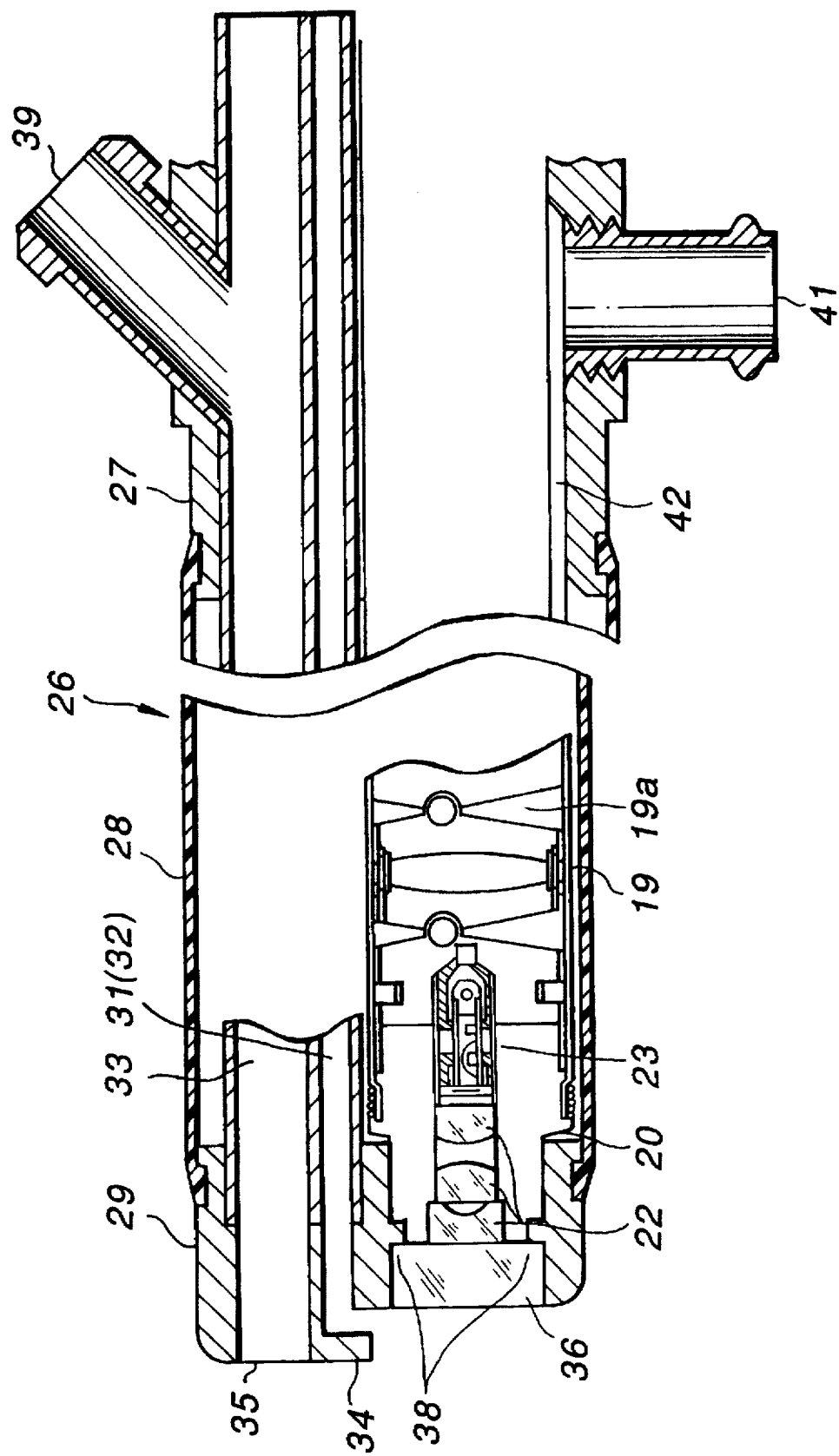

The control portion 12 has a bending control knob 21 to drive a bending block 19a of the bending portion 19 shown in FIG. 7 by operating the bending-control knob 21, resulting in the bending portion 19 to be bent, for example, vertically and laterally. The control portion 12 further comprises an air/water supply switch, a suction switch, and an image change-over switch and so forth to supply air/water, suck the same and freeze the image.

Furthermore, an object optical system 22 and an irradiation optical system 37 (see FIG. 8) are disposed in the leading portion 20 of the insertion portion 14 as shown in FIG. 7. Moreover, the object optical system 22 has, at the rear end portion thereof, an imaging portion 23 on which are mounted a solid-state image sensing device, such as a charge-coupled device for converting an incident optical image into an electric signal and other peripheral circuit devices. The electric signal transmitted from the solid-state image sensing device is received by the video processor 5 via the cable 16 extending from the side portion of the connector 15 disposed at the trailing end of the universal cord 13.

The cover 1 is, as shown in FIG. 6, composed of a control-portion cover 24, a universal cord cover portion 25 and an insertion-portion cover 26 for respectively covering the control potion 12 of the cover-type endoscope 2, the universal cord 13 and the insertion portion 14. Furthermore, the insertion-portion cover 26 is composed of a control-portion fixing joint portion (hereinafter called a "joint portion") 27, a cover leading portion 29, and an insertion-portion cover outer case 28 made of a flexible material and hermetically connected between the joint portion 27 and the cover leading portion 29 to cover the insertion portion 14 of the cover-type endoscope 2 from an external environment. The control-portion cover 24, the universal-cord cover portion 25 and the insertion-portion cover 26 are bound by a band member 30 and the remainder portions are collected so that the cover-type endoscope 2 is covered by the cover 1 hermetically to prevent liquid invasion.

The control-portion cover 24 and the universal-cord cover portion 25 are made of a synthetic resin such as polyurethane, polyester or silicon. The insertion-portion cover 26 is arranged so that its joint portion 27 and the cover leading portion 29 are made of, for example, hard synthetic resin.

The insertion-portion cover outer case 28 is made of, for example, a synthetic resin and is arranged to be made of the same material having an equal thickness for the overall length thereof, thus resulting in maintaining the flexibility of the flexible portion 18 of the cover-type endoscope 2.

The insertion-portion cover 26 includes three flexible tubes, that is, an air supply tube 31, a water supply tube 32 and a suction tube 33. The leading portions of the air supply tube 31 and the water supply tube 32 are connected to an air-supply/water-supply nozzle 34 disposed at the cover leading portion 29. The leading portion of the suction tube 33 is connected to a forceps outlet port 35 also serving as a suction port.

Figure 8:
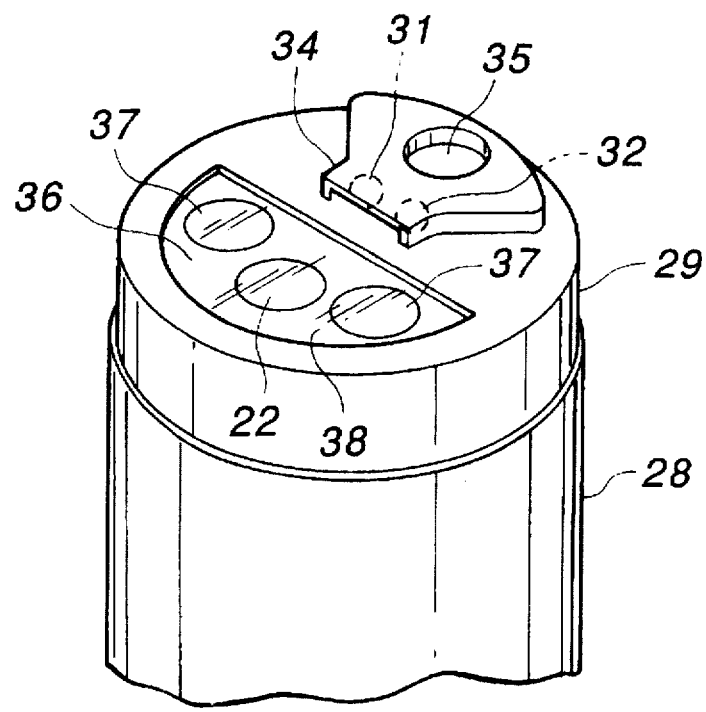
Figure 9:
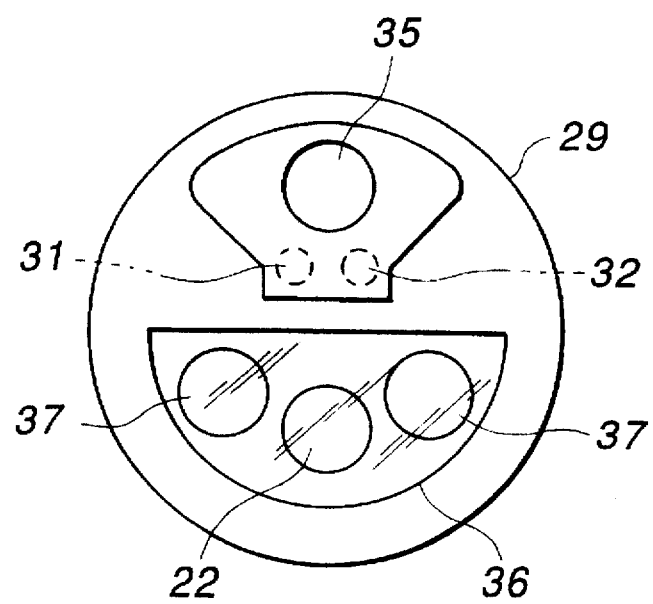

The air-supply/water-supply nozzle 34 has an opening at the leading portion thereof, the opening facing the outer surface of a transparent cover glass 36 formed into a semicircular shape to serve as an observation window. As shown in FIGS. 8 and 9, the cover glass 36 is fitted in a fastening portion 38 formed into a recess disposed to correspond to the irradiating optical system 37 and the object optical system 22 disposed in the leading portion 20 of the cover-type endoscope 2. The cover glass 36 is fixed and bonded hermetically to prevent liquid invasion at the side surface and the bottom surface thereof.

In this case, a channel-provided endoscope cover 400 structured similarly to the cover 1 and having no fastening portion 38 has an arrangement that a cover glass 403 serving as the observation window is bonded to the outer surface of the cover leading portion 401 facing the opening formed in the leading portion of an air-supply/water-supply nozzle 402, causing a necessity of performing an alignment to the leading portion 411 of the cover-type endoscope 410. What is worse, the size of a surface 404 for bonding cannot be enlarged satisfactorily, and delicate care is necessary that a projection of the cover glass 403 does not injure the body cavity at the time of the inspection by making use of the endoscope.

Since the channel-provided endoscope cover 1 according to this embodiment has the fastening portion 38 in the cover leading portion 29 to receive the cover glass 36 serving as the observation window, the alignment to the leading portion 20 of the cover-type endoscope 2 to be fastened to the cover 1 can easily be performed. Moreover, the cover glass 36 can be bonded firmly, resulting in reliable liquid hermetical structure. In addition, the omission of the projection portions from the cover glass 36 enables a safety endoscope inspection to be performed.

The base portions of the air supply tube 31, the water supply tube 32 and the suction tube 33 are extended from the joint portion 27 to reach the fluid control device 6 in a state where they are, together with the universal cord 13 of the cover-type endoscope 2, covered with the universal cord cover portion 25. Thus, the base portions are connected to the fluid control device 6. Therefore, the supply of air and water through the air supply tube 31 and the water supply tube 32 enables adherent body fluid or the like on the cover glass 36 to be removed.

Furthermore, a forceps insertion port 39, through which forceps can be inserted, and an expansion-tube joint 41 for connecting an expansion tube 40 fastened to the expander 7 are disposed on the side surface of the joint portion 27. The forceps insertion port 39 is connected to the suction tube 33, while the expansion-tube joint 41 is disposed apart from the forceps insertion port 39 by an angular degree of 90° or more in the radial direction. As a result, use of one of them does not interfere the other.

As shown in FIG. 7, a portion more adjacent to an operator than the joint portion 27 has an endoscope-insertion channel 42 opened for the purpose of inserting/drawing (attaching/detaching) the insertion portion 14 of the cover-type endoscope 2, the endoscope-insertion channel 42 being connected to the expansion-tube joint 41. It should be noted that the "endoscope-insertion channel 42" is a portion resulted by omitting the air supply tube 31, the water supply tube 32 and the suction tube 33 from an internal space surrounded by the cover leading portion 29, the insertion portion cover outer case 28 and the joint portion 27. The endoscope-insertion channel 42 serves as a portion into which the cover-type endoscope 2 is inserted.

All of the covers 1 each structured as described above are sterilized in a packed state, followed by covering the cover-type endoscope 2 with the clean cover 1 and the cover 1 is disposed after the inspection has been completed. On the other hand, the cover-type endoscope 2 is covered with the clean cover 1 and is repeatedly used.

When an inspection with the endoscope-cover-type endoscope 3 is performed, the insertion facility into the body cavity does not deteriorate because the insertion-portion cover outer case 28 of the cover 1 for covering the flexible portion 18 and the bending portion 19 of the cover-type endoscope 2 is made of the same material and has the equal thickness for the overall length to have equal flexibility that does not deteriorate the flexibility of the flexible portion 18 of the cover-type endoscope 2. In place of the cover-type endoscope 2, the cover 1 can be adapted to another cover-type endoscope, the bending portion of which has a different length, resulting in also maintaining the insertion facility.

Since the conventional cover has been arranged adaptable to a variety of cover-type endoscopes, the lengths of the bending portions of which are different, no particular consideration has not been given to the flexibility of the portion of the cover for covering the insertion portion of the cover-type endoscope. In particular, the flexibility of the portion of the endoscope cover with channels having a channel for a curing tool or a channel for an air/water supply pipe and the like becomes nonuniform to overcome the difficulty in cleaning and disinfecting the endoscope, resulting in a fear of deterioration in the insertion facility into the body cavity at the time of an inspection with the endoscope. However, use of the cover 1 according to the present invention enables excellent operation facility to be obtained while maintaining insertion facility into the body cavity.

Furthermore, the cover 1 covering any one to all of the three tubes, that is, the air supply tube 31, the water supply tube 32 and the suction tube 33 is made of the same material and has the uniform thickness for its overall length to realize the uniform flexibility. Therefore, the flexibility of the flexible portion 18 of the cover-type endoscope 2 can be taken advantage when the cover 1 is fastened. As a result, further satisfactory operation facility can be obtained with the endoscope.

Since the cover 1 has the uniform flexibility in its portion for covering the flexible portion 18 and that for covering the bending portion 19 of the cover-type endoscope 2, the expected bending performance of the cover-type endoscope cannot deteriorate even if the cover 1 is used to cover various cover-type endoscopes each incorporating the bending portion having a different length.

Figure 10:
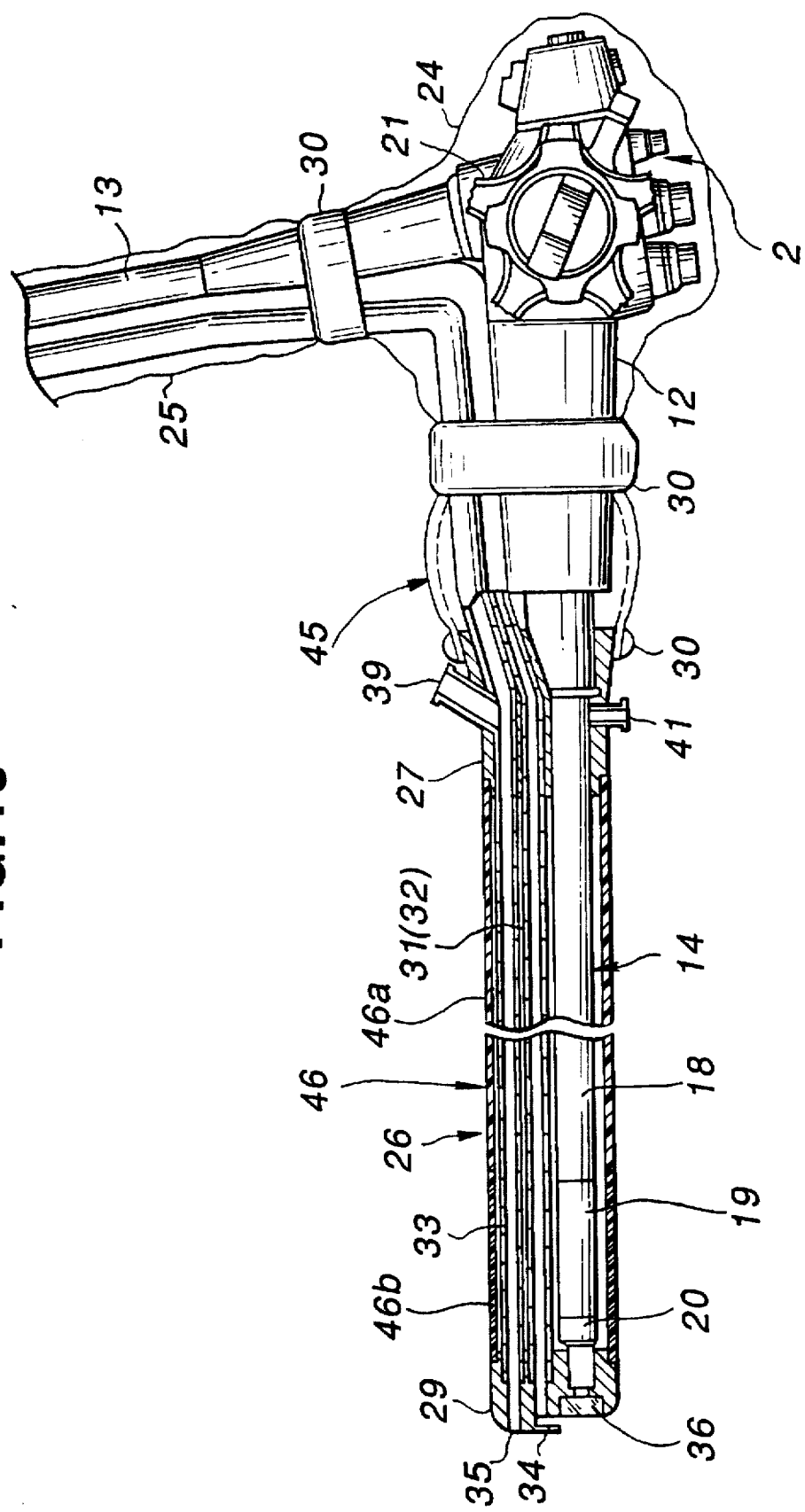
FIGS. 10 and 11 illustrate a second embodiment of the present invention.
Figure 11:
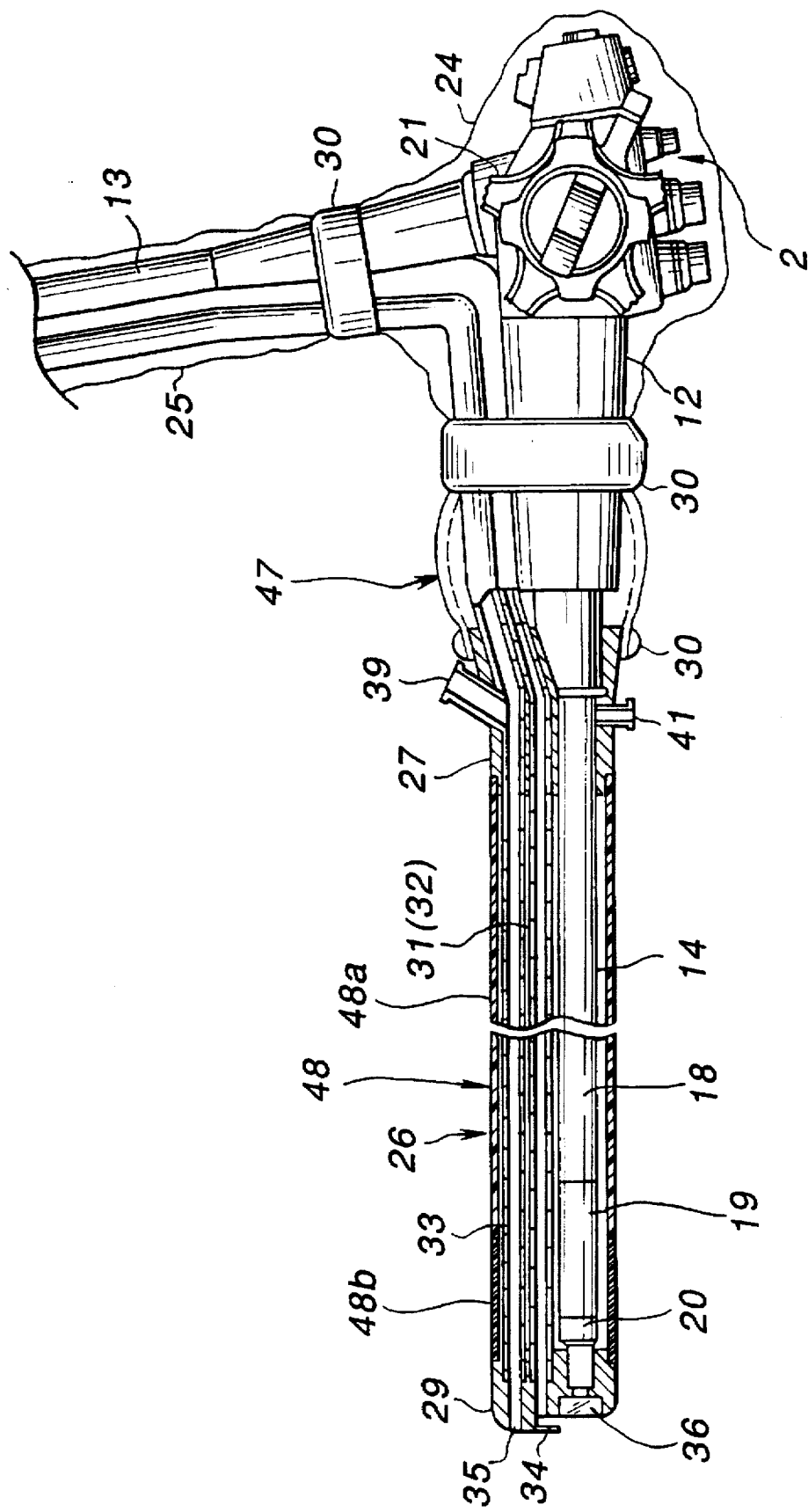

FIGS. 10 and 11 illustrate a second embodiment of the present invention. The same elements as those according to the first embodiment are given the same reference numerals, and their descriptions, therefore, are omitted here.

In contrast with the cover 1 according to the first embodiment that has the insertion portion cover outer case 28 having the uniform flexibility for the overall length to be adaptable to various cover-type endoscopes comprising the bending portions and flexible portions having different lengths, the cover according to this embodiment is adaptable to a case where the range of the lengths of the bending portion and the flexible portion of the cover-type endoscope is limited.

The cover according to this embodiment has an insertion-portion cover outer case formed by, in the axial direction, varying the mixture ratio of plural types of thermoplastic elastomers each having different hardness. An insertion-cover outer case 46 of a cover 45 shown in FIG. 10 has different flexibility at a position corresponding to the flexible portion 18 disposed in front of the bending portion 19 of the cover-type endoscope 2. An insertion-portion cover outer case 48 of a cover 47 shown in FIG. 11 has different flexibility at a position corresponding to the bending portion of the cover-type endoscope.

The insertion-portion cover outer case 46 shown in FIG. 10 is arranged so that a cover outer case 46a corresponding to the flexible portion 18 of the cover-type endoscope 2 contains a lower ratio of a relatively hard thermoplastic elastomer but contains a higher ratio of relatively flexible thermoplastic elastomer so that flexibility which does not deteriorate the flexibility of the flexible portion 18 is secured. Furthermore, a cover outer case 46b corresponding to a portion more forward than the bending portion 19 of the cover-type endoscope 2 contains a higher ratio of relatively hard thermoplastic elastomer so that flexibility of a degree that does not obstruct the bending operation of the bending portion 19 is secured.

Also the insertion-portion cover outer case 48 shown in FIG. 11 comprises the cover outer case 48b corresponding to a portion more forward than the bending portion 19 of the cover-type endoscope 2 contains a higher ratio of relatively hard thermoplastic elastomer so that flexibility of a degree that does not obstruct the bending operation of the bending portion 19 is secured. Furthermore, the cover outer case 48a corresponding to a portion adjacent to an operator contains a lower ratio of a relatively hard thermoplastic elastomer but contains a higher ratio of relatively soft thermoplastic elastomer so that flexibility which does not deteriorate the flexibility of the flexible portion 18 is secured.

Also according to this embodiment, similarly to the first embodiment, excellent facility can be obtained in operating the endoscope while maintaining satisfactory insertion facility into the body cavity at the time of performing an inspection by using the endoscope. Furthermore, a proper selection of the combination of the cover 45 or 46 and the insertion portion 14 of the cover-type endoscope 2 will enable desired flexibility as the cover-type endoscope to be obtained.

By further changing the flexibility of each of the air supply tube 31, the water supply tube 32 and the suction tube 33 respectively disposed in the corresponding covers 45 and 47 to correspond to the insertion-portion cover outer cases 46 and 48, the flexibility of the flexible portion 18 of the cover-type endoscope 2 can be exhibited at the time of fastening the covers. Therefore, further satisfactory facility can be obtained in operating the endoscope.

Although the arrangements shown in FIGS. 10 and 11 are made so that the flexibilities of the insertion-portion cover outer cases 46 and 48 are changed in two steps, the flexibility may be changed in two or more steps or it may be changed in a step-less manner.

FIGS. 12 to 24 illustrate a third embodiment of the present invention.

Figure 12:
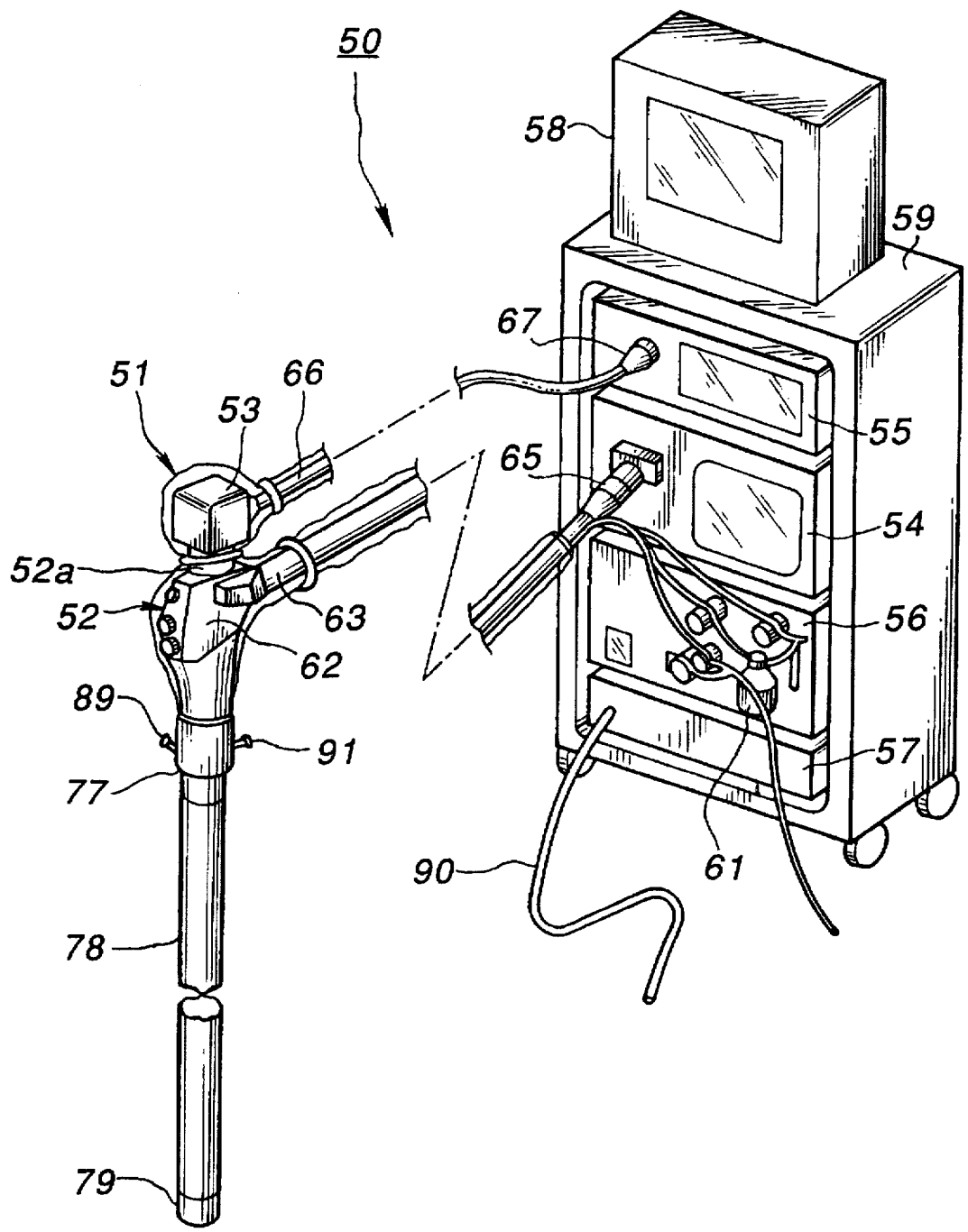
FIGS. 12 to 24 illustrate a third embodiment of the present invention.

Referring to FIG. 12, reference numeral 50 represents an endoscope apparatus. The endoscope apparatus 50 is arranged so that a channel-provided endoscope cover (hereinafter abbreviated to a "cover") 51 covers a cover-type endoscope 52, which is an optical endoscope, and a video camera 53 which is an external camera fastened to an ocular portion 52a of the cover-type endoscope 52. Thus, the cover-type endoscope 52 and the video camera 53 do not need to be cleaned and disinfected after an inspection has been performed by using the endoscope.

A variety of peripheral devices, such as a light source device 54, a fluid control device 56 and a channel-provided endoscope cover expander (hereinafter called an "expander") 57 are connected to the cover-type endoscope 52. Furthermore, a video processor 55 and a monitor 58 and the like are connected to the video camera 53. Among the foregoing peripheral devices, the light source device 54, the video processor 55, the fluid control device 56 and the expander 57 are accommodated in a cart, while the monitor 58 is mounted on the ceiling plate of a cart 59.

The light source device 54 supplies irradiation light to the cover-type endoscope 52. The video processor 55 converts, into a standard video signal, a signal supplied from the video camera 53 including a solid-state image sensing device such as a charge-coupled device to output the video signal to the monitor 58. The monitor 58 receives the video signal to display an endoscope image.

The fluid control apparatus 56 supplies air/water through a tubular passage disposed in the cover 51 and to be described later. Therefore, a water supply source 61 and an air supply source (omitted from illustration) are disposed in the fluid control device 56. The tubular passage connected to the water supply source 61 and the air supply source (omitted from illustration) is controlled by an electromagnetic valve so that they are opened/closed. The expander 57 supplies air to the cover 51 to expand the cover 51 so that the cover 51 can easily be fastened/removed to and from the cover-type endoscope 52.

The cover-type endoscope 52 is structured substantially similarly to a conventional endoscope for use without a cover, the cover-type endoscope 52 comprising a large-diameter control portion 62 having an air/water supply switch and a suction switch and the like, a universal cord 63 extending from the control portion 62 and an elongated insertion portion 64 (see FIG. 14) extending from the base portion of the control portion 62. An ocular portion 62a with which a visual inspection can be performed is disposed in the rear end portion of the control portion 62.

The cover-type endoscope 52 is detachably connected to the light source device 54 via a connector 65 disposed in the trailing portion of the universal cord 62. The video camera 53 is detachably connected to the video processor 55 via a signal connector 67 disposed at the trailing end of a camera cable 66.

Figure 14:
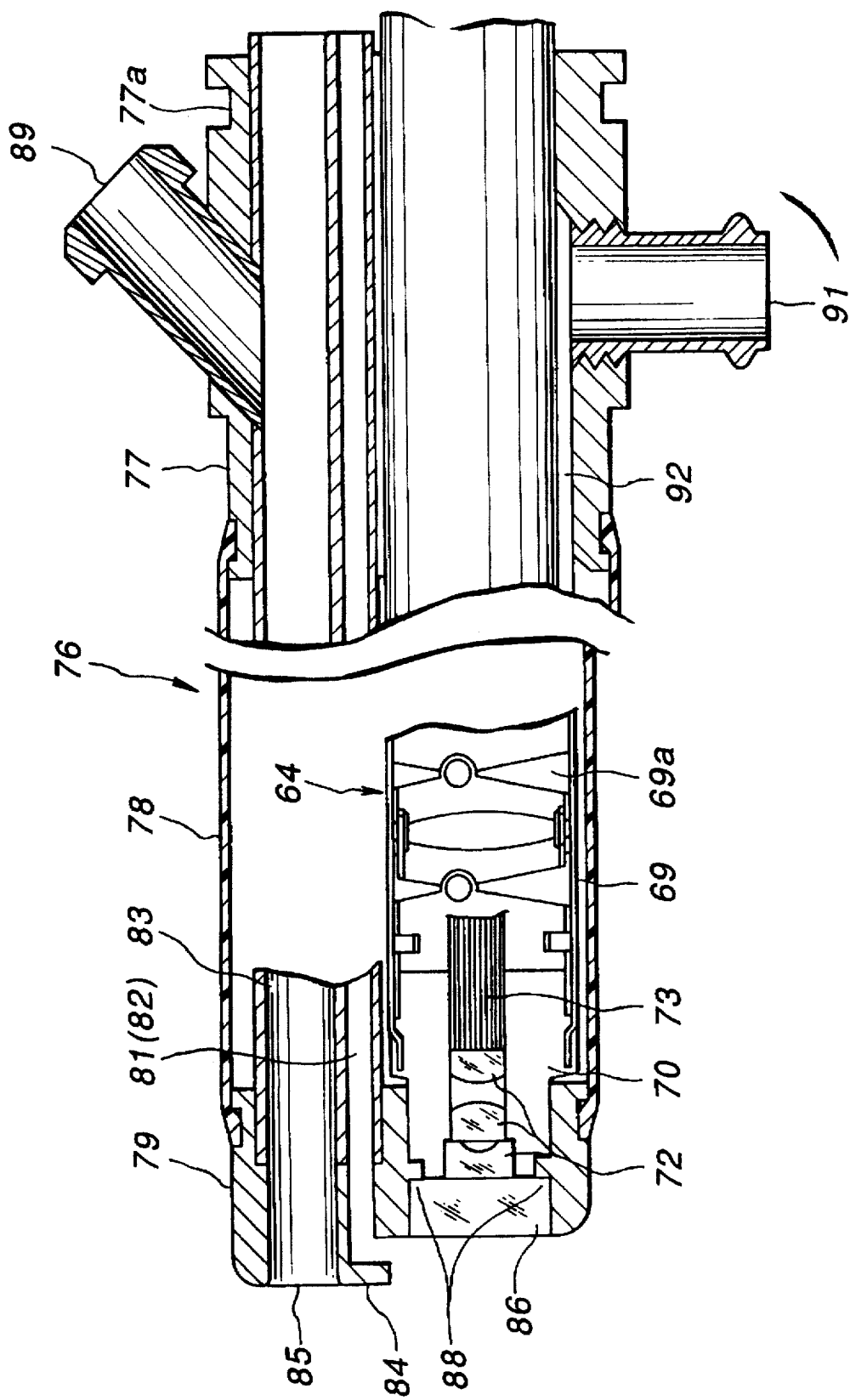

The insertion portion 64 of the cover-type endoscope 52 is, as shown in FIG. 14, composed of a flexible portion made of a flexible tube (omitted from illustration), a bending portion 69 permitted to be bent, a hard leading portion 70 having a semicircular cross sectional shape and arranged to be fastened to a cover leading portion 79 of the cover 51 to be described later which are disposed in this sequential order when viewed from the base portion of the control portion 62 toward the leading portion.

The bending portion 69 includes a plurality of bending blocks 69a which are operated when a bending control knob 71 (see FIG. 22) fastened to the side portion of the control portion 62 so that the bending portion 69 is bent, for example, vertically and laterally.

The warp control knob 71 is, as described later, fastened after the control portion 62 has been covered with the cover 51. The bending control knob 71 is a disposable type knob that is disposed after an inspection with the endoscope has been completed or a knob which is again used followed by cleaning and disinfecting after the inspection with the endoscope has been completed.

The leading portion 70 has an object optical system 72 and an irradiation optical system 87 (see FIG. 15) therein. Furthermore, an image guide 73 comprising an optical fiber bundle is disposed in the rear end portion of the object optical system 72. The trailing end of the image guide 73 faces an ocular optical system disposed in the ocular portion 62a and omitted from illustration. Therefore, an electric signal transmitted from the video camera 53 fastened to the ocular portion 62a is received by the video processor 55 via the camera cable 66.

Figure 13:
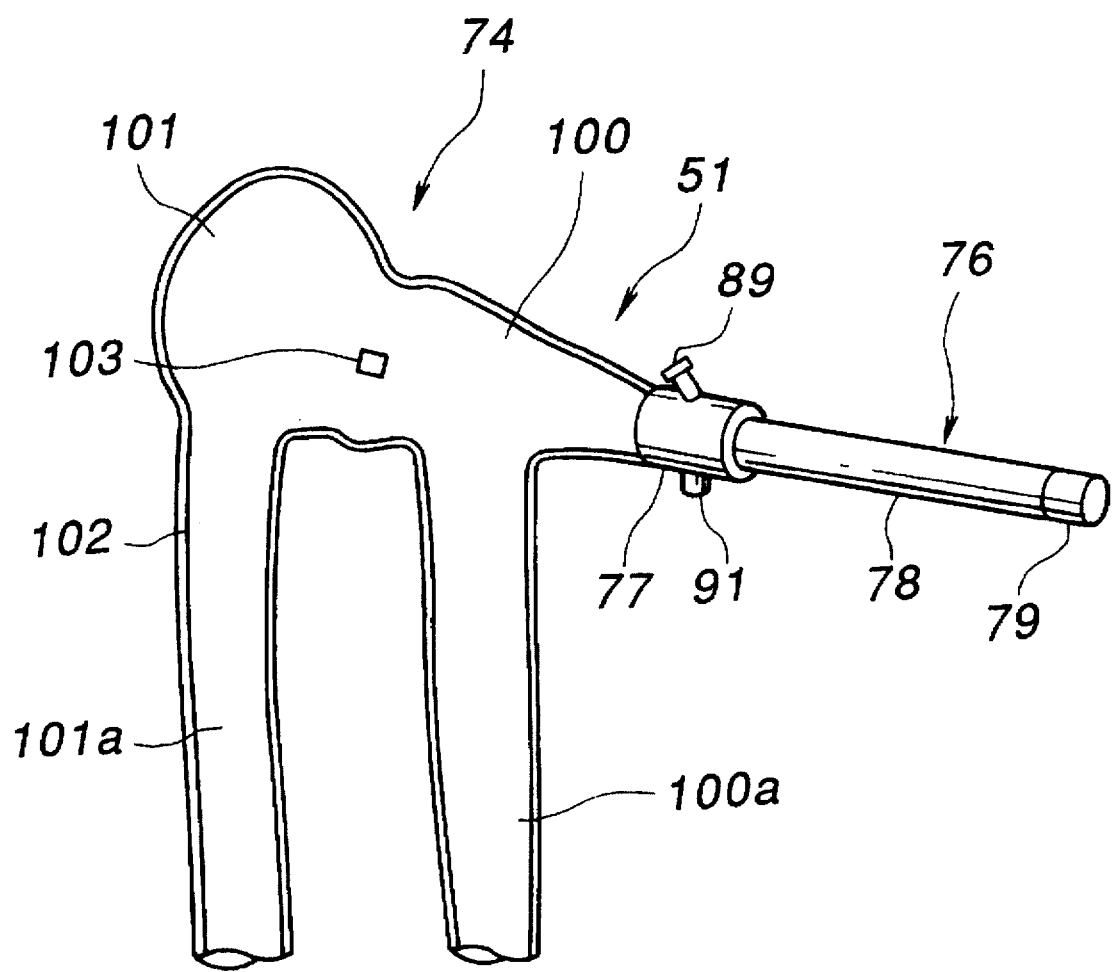

On the other hand, the cover 51 is, as shown in FIG. 13, composed of: a control portion cover 74 for covering the control portion 62 of the cover-type endoscope 52 while also covering the universal cord 63, the video camera 53 and the camera cable 66; and an insertion-portion cover 76 for covering the insertion portion 64 of the cover-type endoscope 52. Furthermore, the insertion-portion cover 76 is composed of: a control-portion fixing joint portion (hereinafter abbreviated to a "joint portion") 77 for fixing the control portion 62 of the cover-type endoscope 52; a cover leading portion 79; and a flexible insertion portion cover outer case 78 hermetically joined between the joint portion 77 and the cover leading portion 79 to insulate the insertion portion 64 of the cover-type endoscope 52 from the external environment.

As shown in FIG. 14, the insertion-portion cover 76 includes an air supply tube 81, a water supply tube 82 and a suction tube 83. The leading portions of the air supply tube 81 and the water supply tube 82 are connected to an air-supply/water-supply nozzle 84 disposed at the cover leading portion 79. The leading portion of the suction tube 83 is connected to a forceps outlet port 85 also serving as a suction port.

Figure 15:
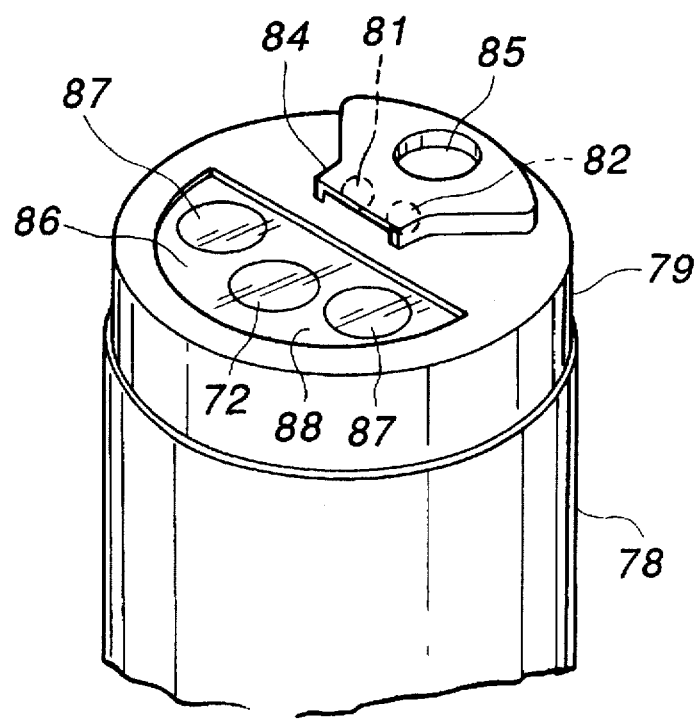
Figure 16:
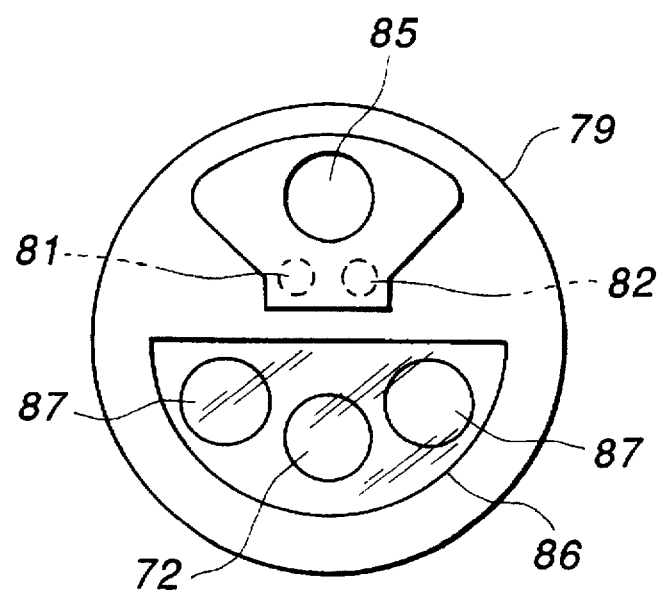

The air-supply/water-supply nozzle 84 has an opening at the leading portion thereof, the opening facing the outer surface of a transparent cover glass 86 formed into a semicircular shape to serve as an observation window. As shown in FIGS. 15 and 16, the cover glass 86 is fitted in a fastening portion 88 formed into a recess disposed to correspond to the irradiating optical system 87 and the object optical system 72 disposed in the leading portion 70 of the cover-type endoscope 52. The cover glass 86 is fixed and bonded hermetically to prevent liquid invasion at the side surface and the bottom surface thereof.

The base portions of the air supply tube 81, the water supply tube 82 and the suction tube 83 are extended from the joint portion 77 to reach the fluid control device 56 in a state where they are, together with the universal cord 63 of the cover-type endoscope 52, covered with the operation-portion cover 74. Thus, the base portions are connected to the fluid control device 56. Therefore, the supply of air and water through the air supply tube 81 and the water supply tube 82 enables adherent body fluid or the like on the cover glass 86 to be removed.

Furthermore, a forceps insertion port 89, through which forceps can be inserted, and an expansion-tube joint 91 for connecting an expansion tube 90 fastened to the expander 57 are disposed on the side surface of the joint portion 77. The forceps insertion port 89 is connected to the suction tube 83, while the expansion-tube joint 91 is disposed apart from the forceps insertion port 89 by an angular degree of 90° or more in the radial direction. As a result, use of one of them does not interfere the other.

A portion more adjacent to an operator than the joint portion 77 has an endoscope-insertion channel 92 opened for the purpose of inserting/drawing (attaching/detaching) the insertion portion 64 of the cover-type endoscope 52, the endoscope-insertion channel 92 being connected to the expansion-tube joint 91. It should be noted that the "endoscope-insertion channel 92" is a portion resulted by omitting the air supply tube 81, the water supply tube 82 and the suction tube 83 from an internal space surrounded by the cover leading portion 79, the insertion portion cover outer case 78 and the joint portion 77. The endoscope-insertion channel 92 serves as a portion into which the cover-type endoscope 52 is inserted.

The control-portion cover 74 is a bag-like member liquid-hermetically fastened to the trailing end of the joint portion 77, the control-portion cover 74 being made from a sheet-like flexible resin. As shown in FIG. 13, an accommodating portion 101 having a shape substantially adaptable to the outline of the video camera 53 is formed in the rear of an accommodating portion 100. Furthermore, extending cylindrical accommodating portions 100a and 101a formed to be substantially adaptable to the outline of the camera cable 66 and substantially running parallel to each other are formed below the accommodating portions 100 and 101.

Figure 17:
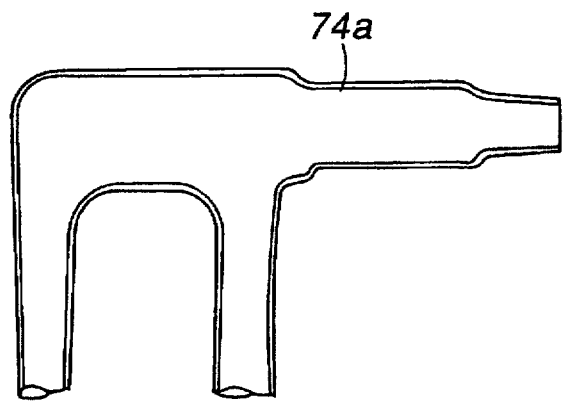
Figure 18:
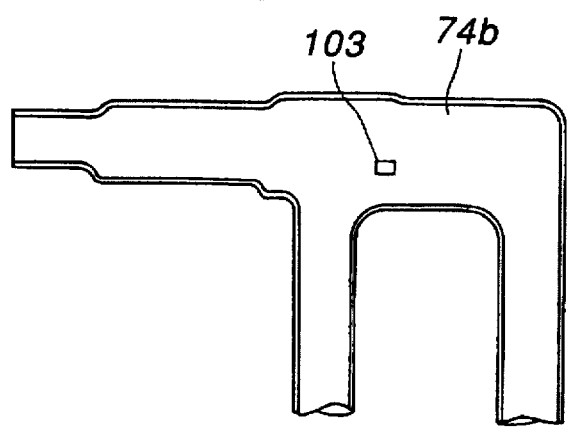
Figure 19:
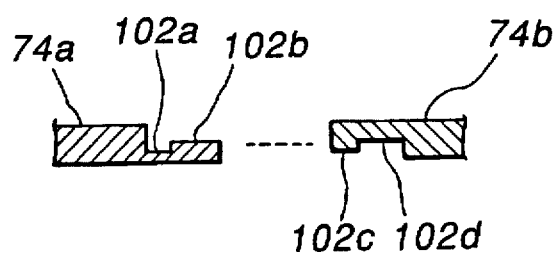

The control-portion cover 74 formed into the bag-like shape can be divided into two sections by a fastener portion 102 in the lengthwise direction of the control portion 62 of the cover-type endoscope 52. By opening the fastening portion 102, the control-portion cover 74 is, as shown in FIGS. 17 and 18, divided into a cover member 74a corresponding to a portion opposing the bending control knob 71 with respect to the control portion 62 of the cover-type endoscope 52 and a cover member 74b having a hole 103 for a bending control shaft 105 to be described later and corresponding to the bending control knob 71.

The fastener portion 102 comprises a groove portion 102a and a projection 102b formed in the outer periphery of the cover member 74a. The fastener portion 102 further comprises a projection 102c and a recess 102d formed in the outer periphery of the cover member 74b. The projection 102c formed adjacent to the cover member 74b has a width somewhat larger than the width of the groove portion 102a adjacent to the cover member 74a. The recess 102d adjacent to the cover member 74b has width somewhat smaller than the width of the projection 102b adjacent to the cover member 74a.

All of the covers 51 each structured as described above are sterilized in a packed state, followed by covering the cover-type endoscope 52 with the clean cover 51 and the cover 51 is disposed after the inspection has been completed. On the other hand, the cover-type endoscope 52 is covered with the clean cover 51 and is repeatedly used.

When the cover-type endoscope 52 and the video camera 53 are covered with the cover 51, the insertion portion 64 of the cover-type endoscope 52 is fastened and secured to the insertion-portion cover 76. Then, the control portion 62 of the cover-type endoscope 52 and the video camera 53 fastened to the ocular portion 62a at the trailing end of the control portion 62 is covered with the other cover member 74a while positioning the cover member 74b of the control-portion cover 74 in a portion to which the bending control knob 71 of the control portion 62 is fastened.

Figure 20:
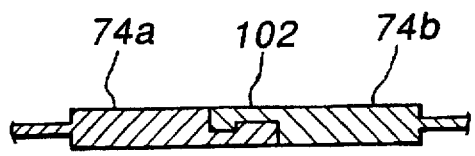

Then, the cover members 74a and 74b are engaged to each other as shown in FIG. 20 by engaging the groove 102a to the projection 102c and engaging the projection 102b to the recess 102d by making use of the elasticity of the material, followed by closing the fastener portion 102 so that the bag-like shape is formed. The overall body of each of the cover members 74a and 74b may have a uniform thickness. By thickening only the outer fastener portion 102, the elasticity of the material can further effectively be utilized.

Figure 21:
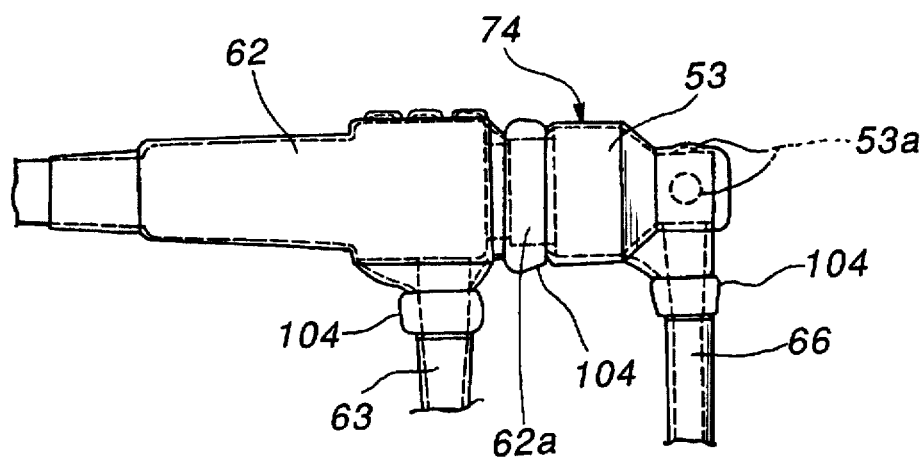
Figure 22:
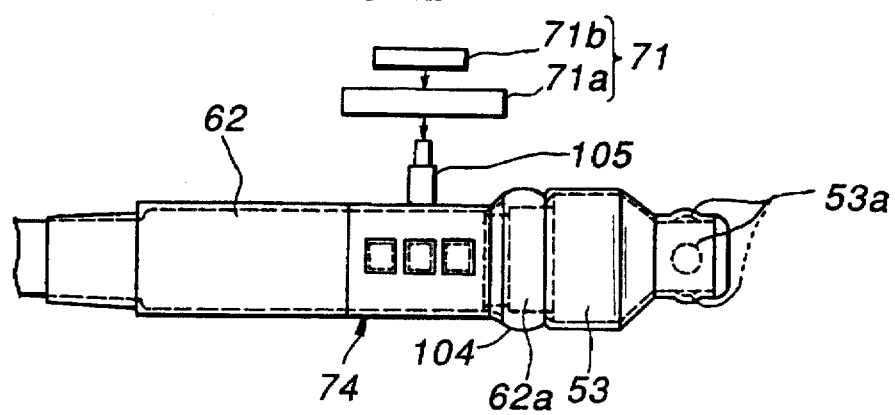

Then, the control-portion cover 74 is liquid-hermetically fixed to the joint portion 77 of the insertion-portion cover 76, followed by binding and fixing the excess portion of the bag-like shape of the control-portion cover 74 to the universal cord 63, the ocular portion 52a and the camera cable 66 by band members 104 as shown in FIG. 21. Further, the bending control knob 71 composed of a vertical-bending control knob 71a and the lateral bending control knob 71b is, as shown in FIG. 22, fastened to the bending control shaft 105 of the control portion 62. Thus, the covering process is completed followed by performing connection to the peripheral devices.

As a result, freezing and releasing switch 53a of the video camera 53 can be operated in a state where the control portion 62 of the cover-type endoscope 52 and the video camera 53 fastened to the ocular portion 62a disposed at the trailing end of the control portion 62 are covered with the control-portion cover 74. Furthermore, the cover-type endoscope 52 and the video camera 53 can always kept clean. Therefore, the necessity of cleaning and disinfecting the video camera 53 can be eliminated as well as cleaning and disinfecting the cover-type endoscope 52 after the inspection with the endoscope has been completed.

Figure 23:
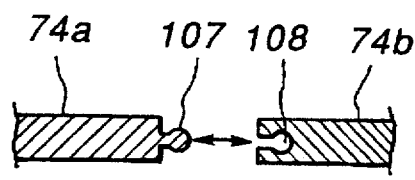
Figure 24:
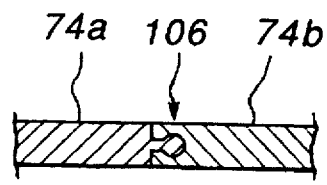

The fastener portion 102 may be replaced by a fastener portion 106 structured as shown in FIGS. 23 and 24. The fastener portion 106 is structured so that a spherical projection 107 is formed on the cover member 74a and a recess 108 to be connected to the projection 107 is formed in the cover member 74b. The fastener portion 106 thus arranged enables a similar operation and effect to be obtained.

Figure 25:
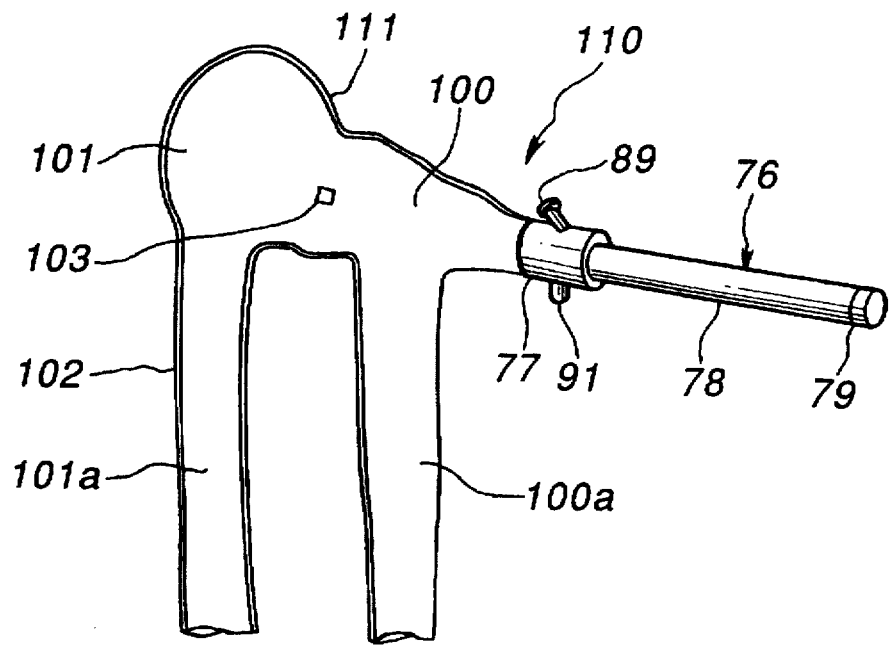
FIGS. 25 and 26 illustrate a fourth embodiment of the present invention.
Figure 26:
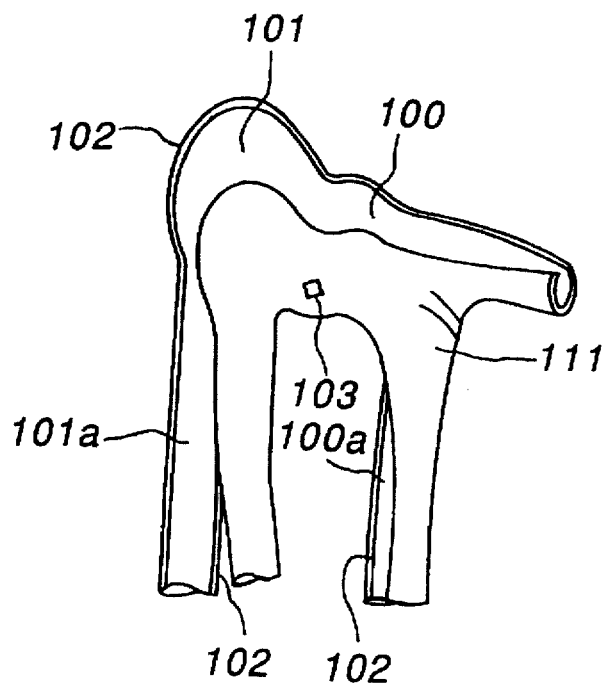

FIGS. 25 and 26 illustrate a fourth embodiment of the present invention. The same elements as those according to the third embodiments are given the same reference numerals and their detailed descriptions are omitted here.

This embodiment has an arrangement that the cover 51 according to the third embodiment is replaced by a cover 110 which is difference in only a control-portion cover 111. The control-portion cover 111 solely forms a bag-like shape.

The control-portion cover 111 has a similar shape to that of the control-portion cover 74 according to the third embodiment as shown in FIG. 25. The control-portion cover 111 has the accommodating portion 100 for accommodating the control portion 62 of the cover-type endoscope 52, the accommodating portion 101 for accommodating the video camera 53, the accommodating portion 100a for accommodating the universal cord 63 and the accommodating portion 101a for accommodating the camera cable 66. However, the position at which the fastener portion 102 is disposed is different from the control-portion cover 74 according to the first embodiment.

That is, the control-portion cover 111 according to this embodiment is able to form the bag-like shape by one element as shown in FIG. 26. By providing the fastener portion 102 except for the side portion of the accommodating portion 100a for accommodating the universal cord 63, a portion of the bag-like shape can be opened.

According to this embodiment, the cover-type endoscope 52 and the video camera 53 can always be kept clean similarly to the third embodiment. Furthermore, the control-portion cover 111 is formed into the bag-like shape by one element, and the bag-like shape can be opened partially. Therefore, attachment and detachment of the cover can easily be performed. Moreover, the control-portion cover 111 cannot be separated into two pieces, resulting in eliminating a fear of missing one of them.

FIGS. 27 to 31 illustrate a fifth embodiment of the present invention.

Figure 30:
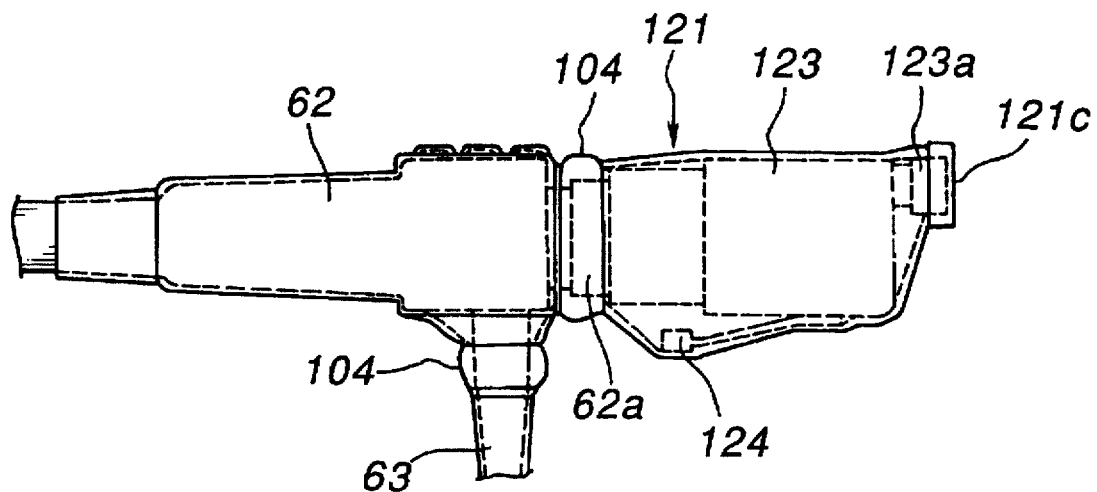
Figure 31:
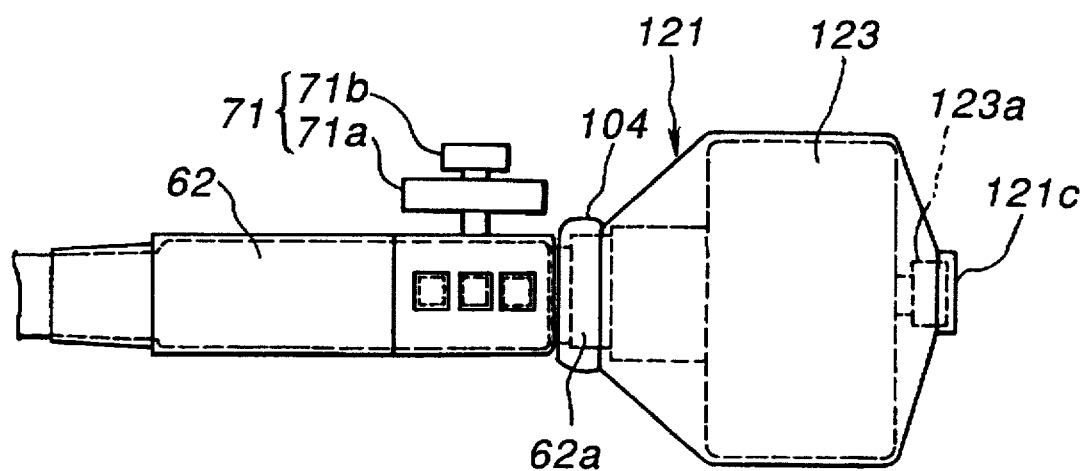

This embodiment has an arrangement that the video camera 53 serving as the external camera according to the third embodiment is replaced by a camera 123 as shown in FIGS. 30 and 31. Furthermore, the control portion 62 of the cover-type endoscope 52 to which the camera 123 is mounted is integrally covered with a cover 120.

Figure 27:
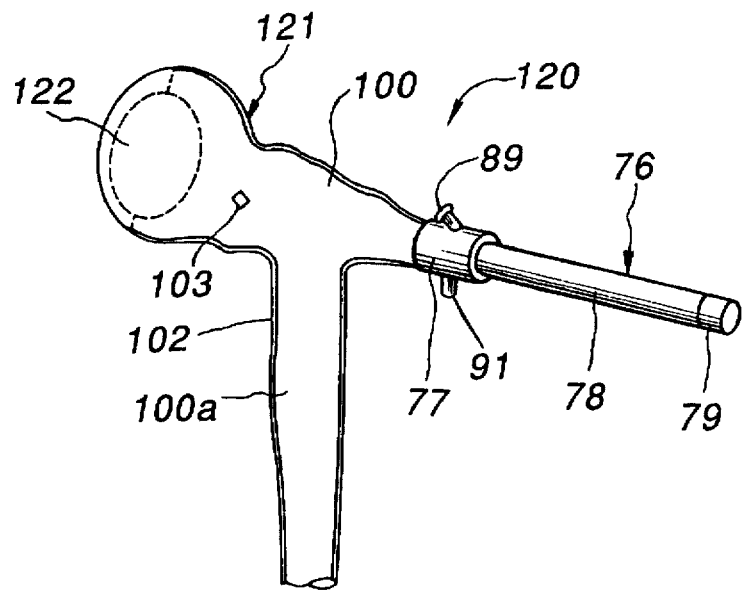
FIGS. 27 to 31 illustrate a fifth embodiment of the present invention.

The cover 120 according to this embodiment is arranged similarly to the cover 51 according to the third embodiment except for only a control-portion cover 121 as shown in FIG. 27. The control-portion cover 121 is formed into a bag-like shape made of a sheet-like flexible resin to be liquid-hermetically fastened to the trailing end of the joint portion 77. An accommodating portion 122 having a shape substantially adaptable to the outline of the camera 123 is formed in the rear of an accommodating portion 1000 having a shape substantially adaptable to the outline of the control portion 62 of the cover-type endoscope 52. Furthermore, a projecting cylindrical accommodating portion 100a having a shape substantially adaptable to the outline of the universal cord 63 is formed in the lower portion of the accommodating portion 100.

Figure 28:
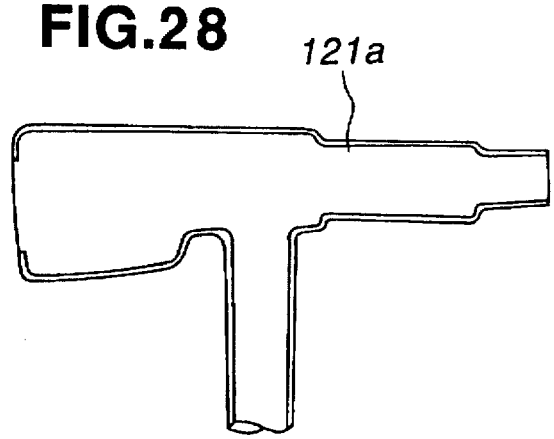
Figure 29:
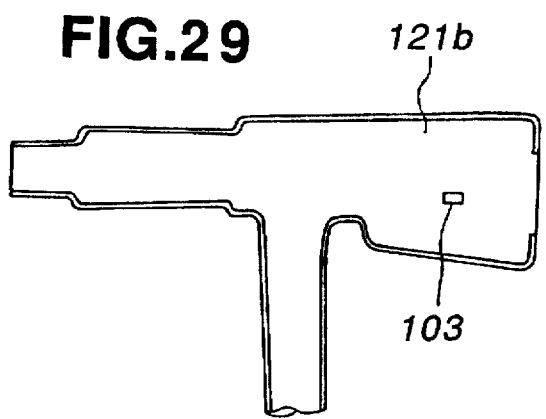

The control-portion cover 121 formed into the bag-like shape can be divided into two sections in the lengthwise direction of the control portion 62 of the cover-type endoscope 52 by the fastener portion 102. By opening the fastening portion 102, the control-portion cover 121 is, as shown in FIGS. 28 and 29, divided into a cover member 121a corresponding to a portion opposing the bending control knob 71 with respect to the control portion 62 of the cover-type endoscope 52 and a cover member 121b having a bending control shaft 105 corresponding to the warp control knob 71. The residual structure is arranged similarly to the third embodiment.

The control-portion cover 121 according to this embodiment is used to cover the cover-type endoscope 52, the camera 123 and a release switch 124 of the camera 123 by closing the fastener portion 102 to form the bag-like shape. Then, the excess portion of the bag-like control-portion cover 121 is bound and fixed to the universal cord 63 and the ocular portion 62a by the band members 104 as shown in FIG. 30. Then, the bending control knob 71 is fastened to the warp control shaft 105 as shown in FIG. 31. Then, an ocular ring 121c is fastened to an ocular portion 123a of the camera 123 behind the control-portion cover 121 to secure the visual field.

Also according to this embodiment, the control-portion 121 is able to integrally cover the control portion 62 of the cover-type endoscope 52 and the camera 123 fastened to the ocular portion 62a disposed at the trailing end of the control portion 62, and, accordingly, the cover-type endoscope 52 and the camera 123 can always be kept clean. Therefore, cleaning and disinfecting can be omitted after the inspection with the endoscope has been completed.

Figure 32:
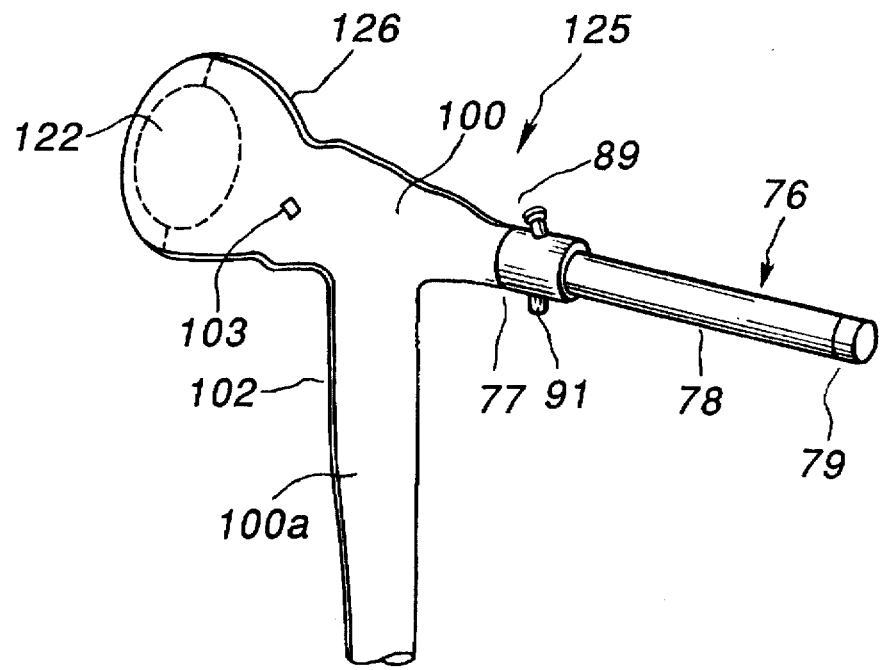
FIGS. 32 and 33 illustrate a sixth embodiment of the present invention.
Figure 33:
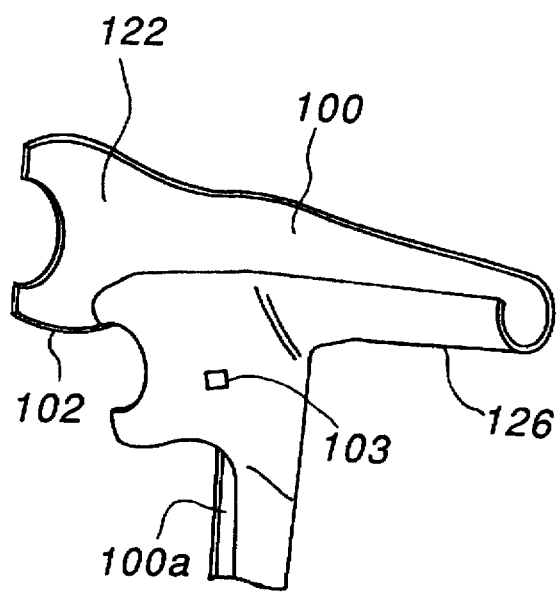

FIGS. 32 and 33 illustrate a sixth embodiment of the present invention.

This embodiment has an arrangement that the cover 120 according to the fifth embodiment is replaced by a cover 125 having a control-portion cover 121 which is solely different from the cover 120. The control-portion cover 126 of the cover 125 is able to form a bag-like shape by only one element.

That is, the control-portion cover 126 is formed into a similar shape to that of the control-portion cover 121 according to the fifth embodiment as shown in FIG. 32. The control-portion cover 126 has the accommodating portion 100 for accommodating the control portion 62 of the cover-type endoscope 52, the accommodating portion 122 for accommodating the camera 73 and the accommodating portion 100a for accommodating the universal cord 63. Furthermore, a portion of the bag-like shape can be opened as shown in FIG. 33 by the fastener portion 102 provided for the control-portion cover 126 except for a portion adjacent to the side portion of the accommodating portion 100a for accommodating the universal cord 63. The residual structures are the same as those according to the fifth embodiment.

Also according to this embodiment, similarly to the fifth embodiment, the cover-type endoscope 52 and the camera 123 can always be kept clean. Furthermore, the control-portion cover 126 is formed into a bag-like shape by one element which can be partially opened. Therefore, the cover can easily be attached and detached, and the control-portion cover 126 is not divided into two pieces, resulting in eliminating a fear of missing one of them.

Although the third to the sixth embodiments each has the arrangement that the channel-provided endoscope cover and the cover-type endoscope are combined, the present invention is not limited to this. The present invention may be adapted to a channel-less endoscope cover. As the cover-type endoscope, an endoscope having a hard insertion portion or a conventional cover-less endoscope may be employed.

Figure 34:
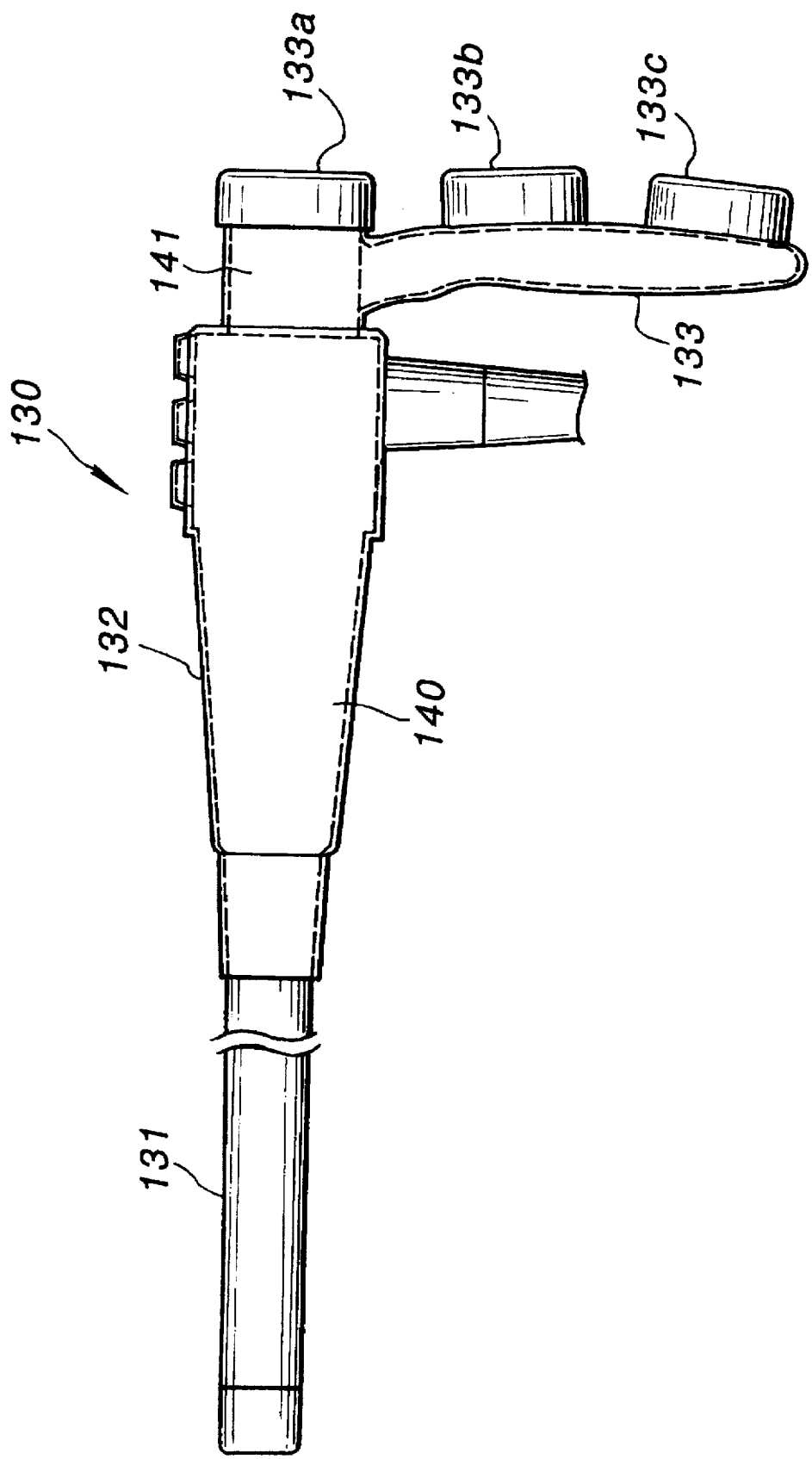
FIG. 34 illustrates a seventh embodiment of the present invention.

FIG. 34 illustrates a seventh embodiment of the present invention.

Generally, an optical endoscope having an ocular portion at the trailing end of the control portion thereof is used to perform an observation by operating a diopter adjustment mechanism of the ocular portion prior to performing the inspection with the endoscope. Also the cover-type endoscope employs a similar structure. Since the cover-type endoscope including the control portion is, however, fully covered with the cover, it has been difficult to adjust the diopter of the ocular portion of the cover-type endoscope in a state where the cover is fastened.

A cover 130 shown in FIG. 34 comprises an insertion-portion cover 131 for covering the insertion portion of a cover-type endoscope, which is an optical endoscope, and a control-portion cover 132 for covering a control portion 140 of the cover-type endoscope. The control-portion cover 132 has an ocular-portion cover 133 for covering an ocular portion 141 formed at the trailing end of the control portion 140.

The ocular-portion cover 133 is formed into a bag-like shape having a size provided with an allowance with respect to the ocular portion 141. Furthermore, a plurality of ocular caps 133a, 133b and 133c each having a diopter lens to serve as an ocular lens for the endoscope are secured or integrally formed, the diopter lenses having different diopters. The provided ocular caps 133a, 133b and 133c are selectively fastened to the ocular portion 143.

By properly selecting the ocular cap 133a, 133b or 133c of the cover 130 and by fastening the selected ocular gap to the ocular portion 141 of the cover-type endoscope in such a manner that the ocular-portion cover 133 having a size provided with an allowance is shifted, the diopter can easily be adjusted even during an operation by using the endoscope.

Figure 35:
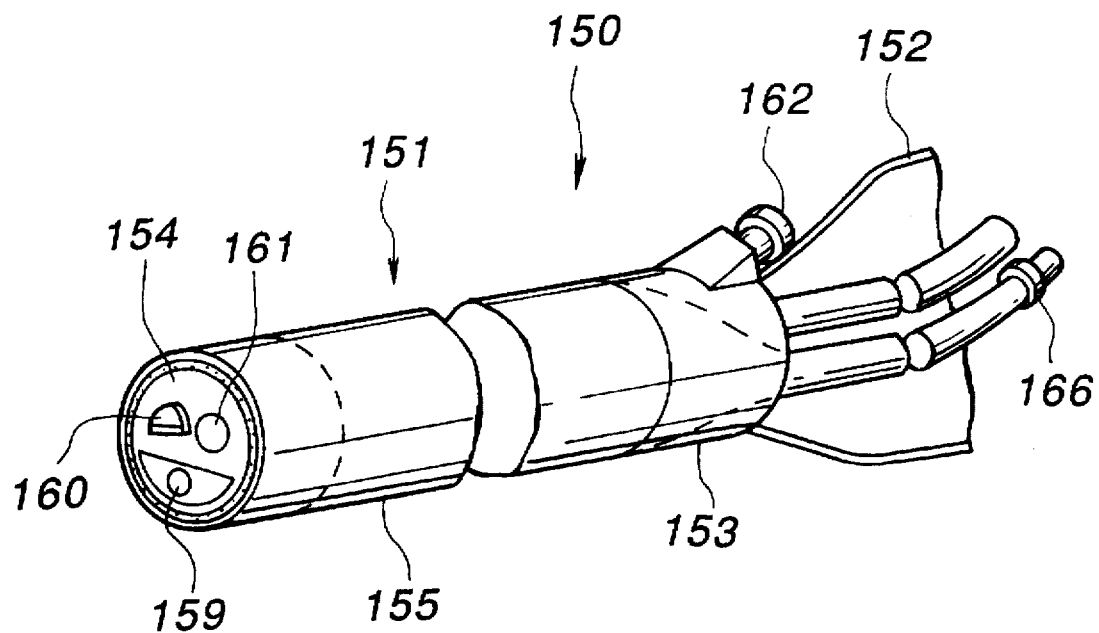
FIGS. 35 to 37 illustrate an eighth embodiment of the present invention.
Figure 36:
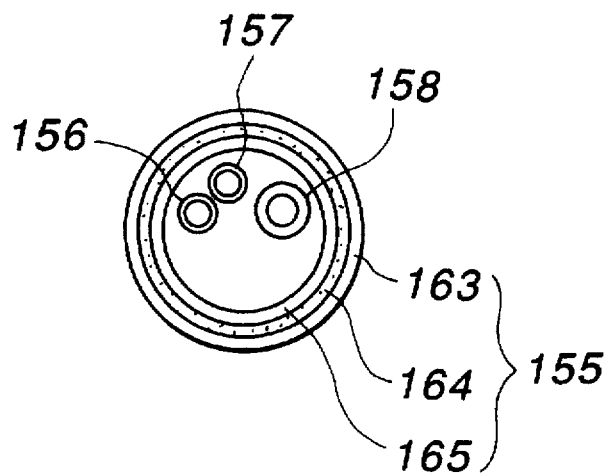
Figure 37:
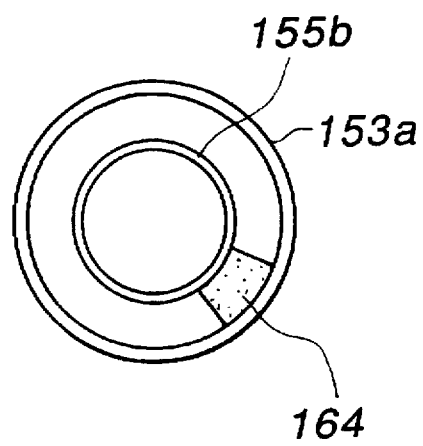

FIGS. 35 to 37 illustrate an eighth embodiment of the present invention.

Hitherto, the cover-type endoscope includes a light guide comprising an optical fiber bundle for propagating irradiation light emitted from a light source device similarly to the cover-less endoscope. Furthermore, a universal cord through which the light guide passes is extended from the control portion of the endoscope. Therefore, the universal cord of the cover-type endoscope must be covered as well as the insertion portion and the control portion, resulting in a complicated work at the time of fastening the cover.

A cover 150 shown in FIG. 35 is adapted to a cover-type endoscope, in particular, a cover-type endoscope, which is an optical endoscope having an ocular portion but having no universal cord. Therefore, the cover 150 comprises an insertion-portion cover 151 for covering the insertion portion of the cover-type endoscope and a control-portion cover 152 for covering the control portion of the cover-type endoscope. In this case, the universal-cord cover portion for covering the universal cord is omitted.

The insertion-portion cover 151 is constituted by a joint portion 153 for fixing the control portion of the cover-type endoscope, a cover leading portion 154, and an insertion-portion cover outer case 155 for hermetically covering the cover leading portion 154 and hermetically connected to the joint portion 153 for the purpose of insulating the insertion portion of the cover-type endoscope from the external environment.

An air supply tube 156, a water supply tube 157 and a suction tube 158 pass through the insertion-portion cover 151 (see FIG. 36). The leading portions of the air supply tube 156 and the water supply tube 157 are connected to air/water supply nozzle 160 facing an observation window 159 of the cover leading portion 154. Furthermore, the leading portion of the suction tube 158 is connected to a forceps outlet port 161 also serving as a suction port of the cover leading portion 154. The tubes 156, 157 and 158 are bound and extended from the trailing end of the insertion-portion cover 151.

The joint portion 153 has, on the side surface thereof, a forceps insertion port 162 which is connected to the suction tube 158 and through which forceps can be inserted, and an expanding tube joint (omitted from illustration) for supplying air for expanding the cover 150 at the time of fastening or removing the cover-type endoscope to the cover 150.

As shown in FIG. 36, the insertion-portion cover outer case 155 is formed into a triple-layer structure composed of, when viewed from the outside, a first layer made of a flexible vinyl tube 163, a second layer filled with an optical fiber bundle 164 for introducing irradiation light, and a third layer made of a flexible vinyl tube 165 similarly to the first layer.

The optical fiber bundle 164 forming the second layer has the emission terminal exposed outside at the cover leading portion 154 as shown in FIG. 35. Furthermore, the optical fiber bundles 164 is bound in one part between an outer tube 153a and an inner tube 153b of the joint portion 153, followed by extending the bundle from the trailing end of the joint portion 153 in such a manner that the bundle is covered with a flexible vinyl tube.

An incident terminal of the optical fiber bundle 163 extended from the trailing end of the joint portion 153 is connected to a light-source connecting joint 166 to introduce irradiation light made incident upon from the light source, followed by emitting irradiation light from the cover leading portion 154. As a result, an observation through an observation window 159 by using the cover-type endoscope fastened to the cover 150 can easily be performed.

That is, the cover 150 includes the light guide, and, accordingly, the light guide can be omitted from the cover-type endoscope to be fastened to the cover 150. Therefore, the universal cord through which the light guide passes can also be omitted. Hence, the universal-cord cover portion for covering the universal cord can be omitted, resulting in simplification of the work for fastening the cover to the cover-type endoscope. As a result, the time taken to fasten the cover can be shortened.

FIGS. 38 to 44 illustrate a ninth embodiment of the present invention.

Hitherto, the structure in which the cover-type endoscope is covered encounters a difficulty in holding the control portion because the control portion of the cover-type endoscope is covered with the control-portion cover made of a sheet-like flexible resin.

Figure 42:
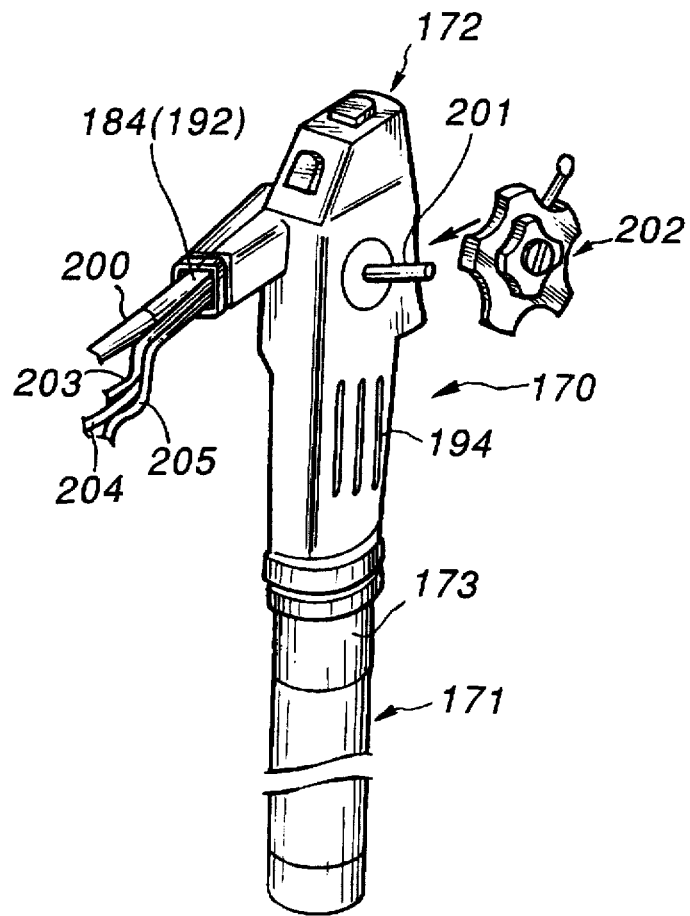

In order to overcome the foregoing problem, a cover 170 shown in FIG. 42 has an insertion-portion cover 171 for covering the insertion portion of the cover-type endoscope and a control-portion cover 172 for covering the control portion of the cover-type endoscope and made of a relatively hard resin, the control-portion cover 172 being connected to the insertion-portion cover 171. As a result, the control-portion cover 172 can easily be held.

Figure 38:
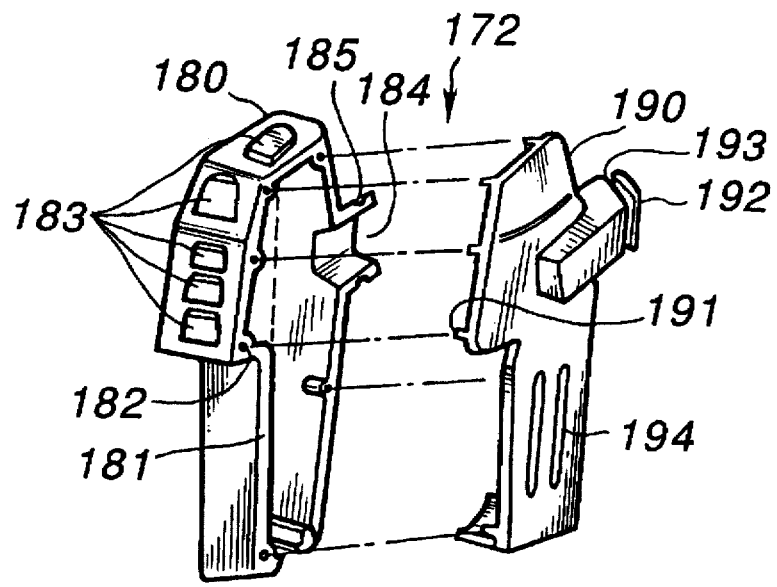
FIGS. 38 to 44 illustrate a ninth embodiment of the present invention.

The control-portion cover 172 is constituted by a cover body 180 and a cover cap 190 to be fixed to the cover body 180 as shown in FIG. 38. A plurality of fixing holes 182 formed in a joining surface 181 of the cover body 180 and projections 191 of the cover cap 190 corresponding to the fixing holes 182 are connected to one another so that the control-portion cover is formed.

The cover body 180 has a switch cover 183 corresponding to a switch of the cover-type endoscope and made of a flexible resin. The residual portion of the cover body 180 is made of a relatively hard plastic resin. Furthermore, the cover body 180 has an opening 184 corresponding to a universal cord 200 extended from the side portion of the control portion of the cover-type endoscope. In addition, a groove portion 185 is formed in the outer periphery of the opening 184 for the purpose of fastening a universal cord cover 210 to be described later.

Figure 39:
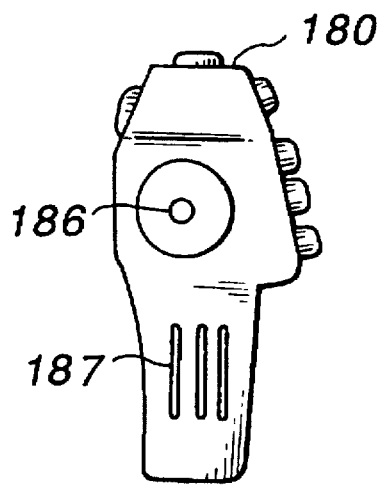

As shown in FIG. 39, the cover body 180 has a hole 186 at a position at which a bending control knob 202 is afterward fastened to a bending control shaft 201 projecting over the control portion of the cover-type endoscope. Furthermore, the holding portion has a slip stopper 187 therein.

On the other hand, the cover cap 190 has an opening 192 to correspond to the universal cord 200 of the cover-type endoscope similarly to the cover body 180. Furthermore, a groove portion 193 is formed on the outer periphery of the opening 192 for the purpose of fastening the universal cord 210. Also the cover cap 190 has a slip stopper 194 formed in the holding portion thereof.

Figure 40:
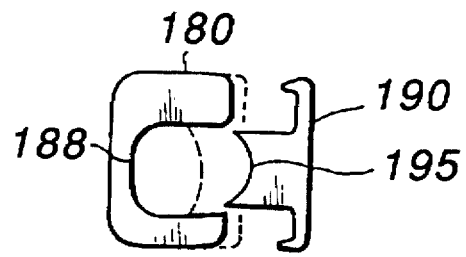
Figure 41:
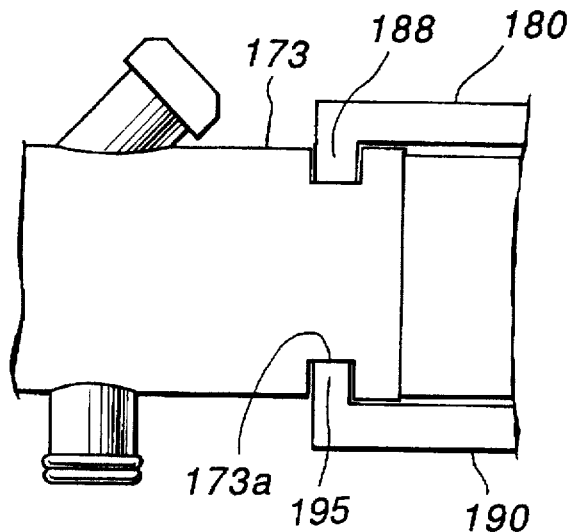

The control-portion cover 172 is connected and fixed to the joint portion 173 of the insertion-portion cover 171. As shown in FIGS. 40 and 41, a first joint portion 188 formed in the cover body 180 and a second joint portion 195 formed in the cover cap 190 form a fastening portion having a diameter smaller than that of a groove 173a formed in the trailing portion of the joint portion 173 to be received and held by the groove 173a.

In a state where the cover-type endoscope is covered with the cover 170 as shown in FIG. 42, an air supply tube 203 adjacent to an operator, a water supply tube 204 adjacent to the operator and a suction tube 205 adjacent to the operator each extending from the joint portion 173 are disposed in the control-portion cover 172. Furthermore, they are, together with the universal cord 200 of the cover-type endoscope, extended through an outlet port formed by the opening 184 of the cover body 180 and the opening 192 of the cover cap 190.

Figure 43:
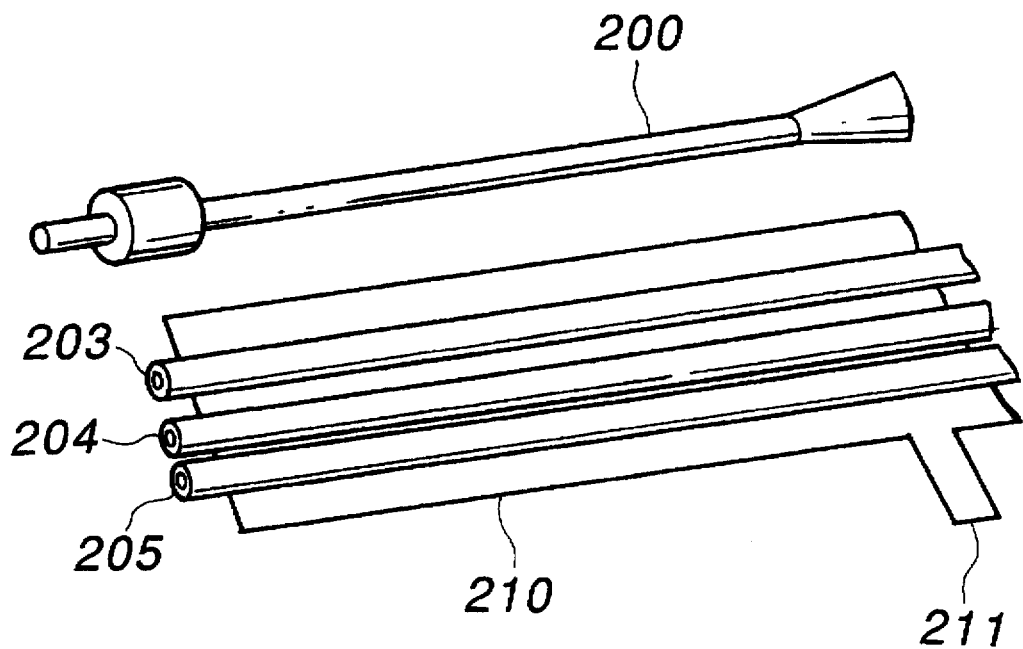

The tubes 203, 204 and 205 and the universal cord 200 are covered with a universal cord cover 210 made of a sheet-like flexible resin as shown in FIG. 43. The universal cord cover 210 is so wound as to cover the tubes 203, 204 and 205 and the universal cord 200. Furthermore, the tubes 203, 204 and 205 are fixed at the end portion of the universal cord 200 by a binding member while branching and extending the tubes 203, 204 and 205.

Figure 44:
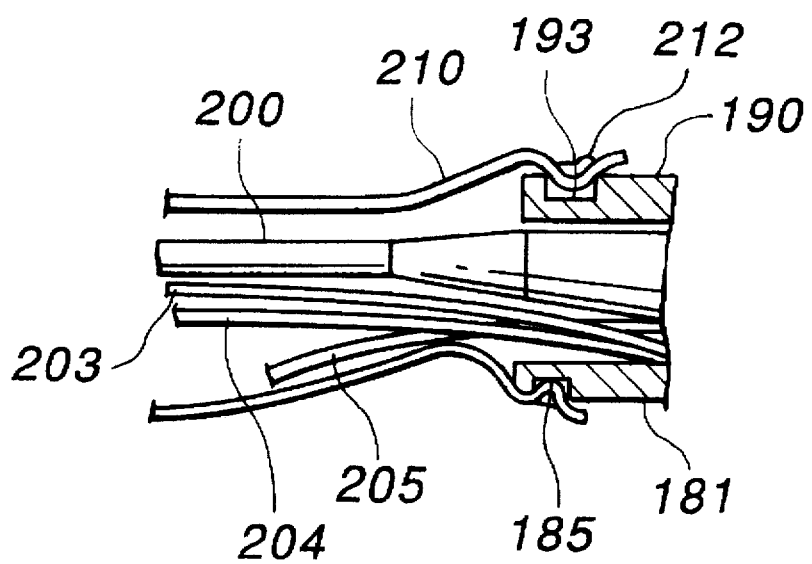

The universal cord cover 210 has, at the substantially end portion thereof, a tag-like binding member 211. The binding member 211 enables the base portion of the universal cord cover 210 to be fastened to the fastening portion formed by the groove portion 185 of the cover body 180 and the groove portion 193 of the cover cap 190 as shown in FIG. 44. Furthermore, the base portion is fixed by a binding member 222 to be connected to the control-portion cover 172. The tubes 203, 204 and 205 branched and extended from the universal cord 210 are connected to the fluid control device for supplying air/water.

Since the control portion of the cover-type endoscope is covered with the control-portion cover 172 made of the relatively hard resin, the control portion can be held significantly easily as compared with a case where the same is covered with a conventional flexible control-portion cover. Therefore, the operation facility can be improved.

Figure 45:
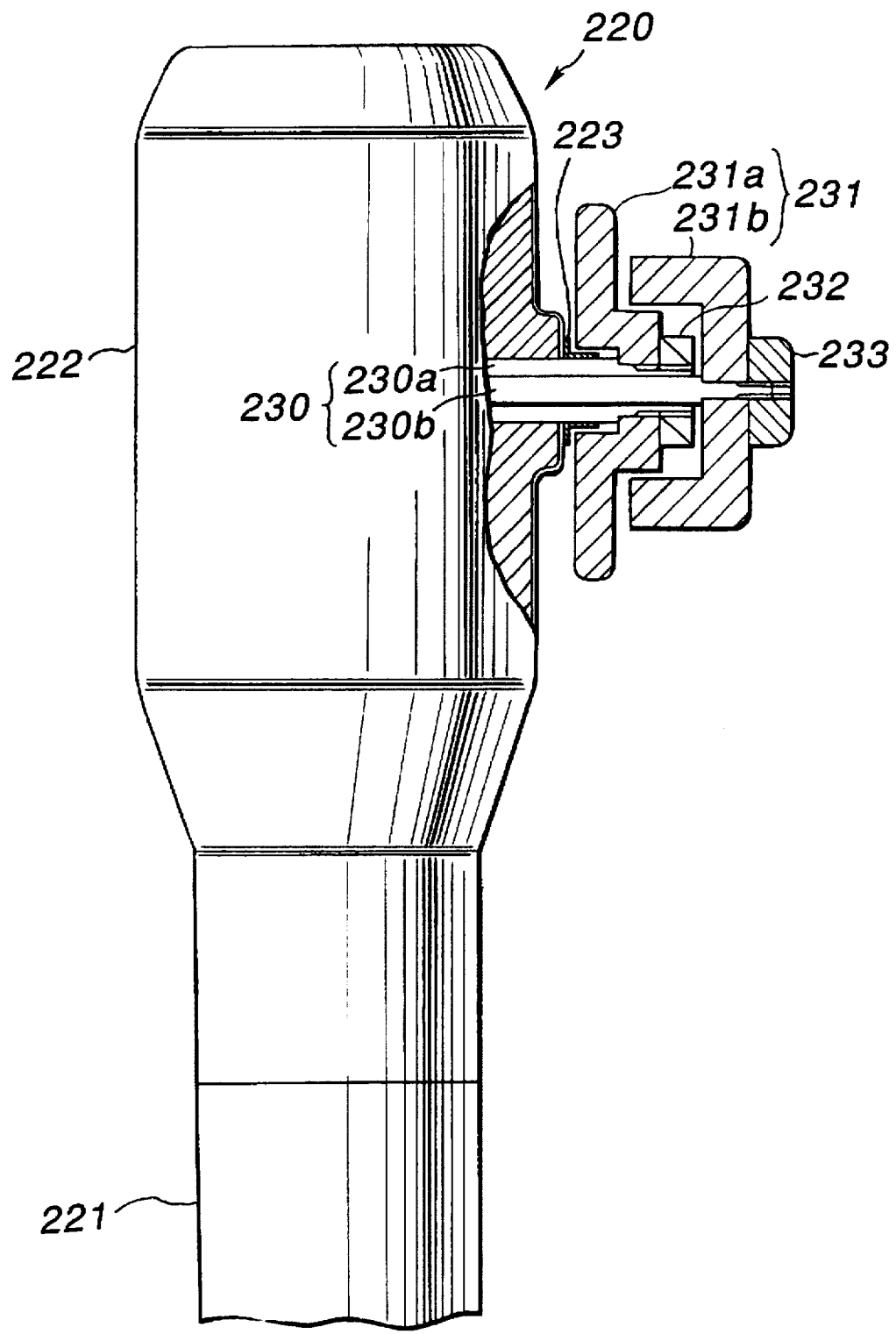
FIG. 45 illustrates a tenth embodiment of the present invention.

FIG. 45 illustrates a tenth embodiment of the present invention.

Figure 1:
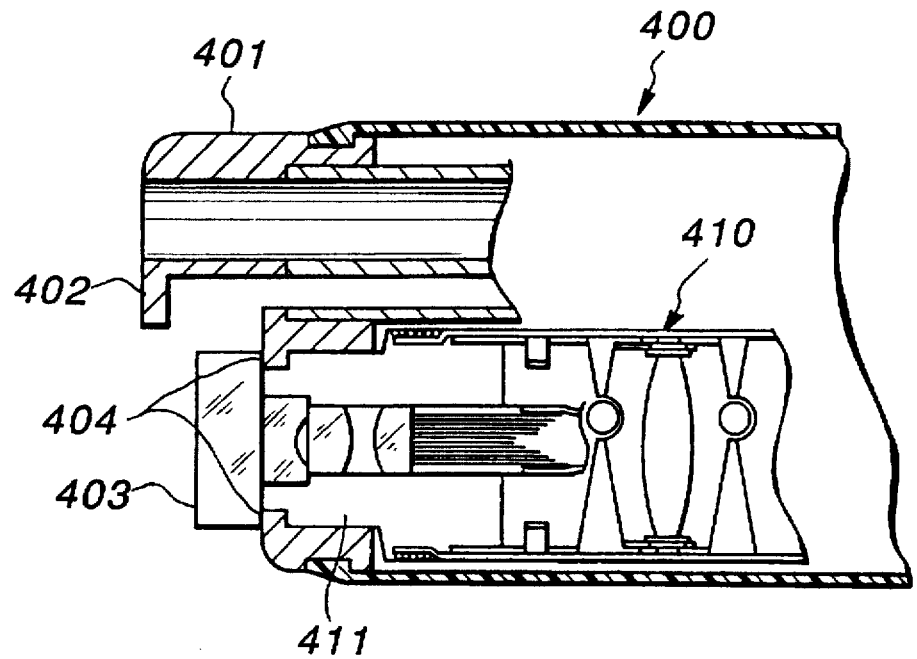
FIGS. 1 to 4 illustrate a related art.
Figure 2:
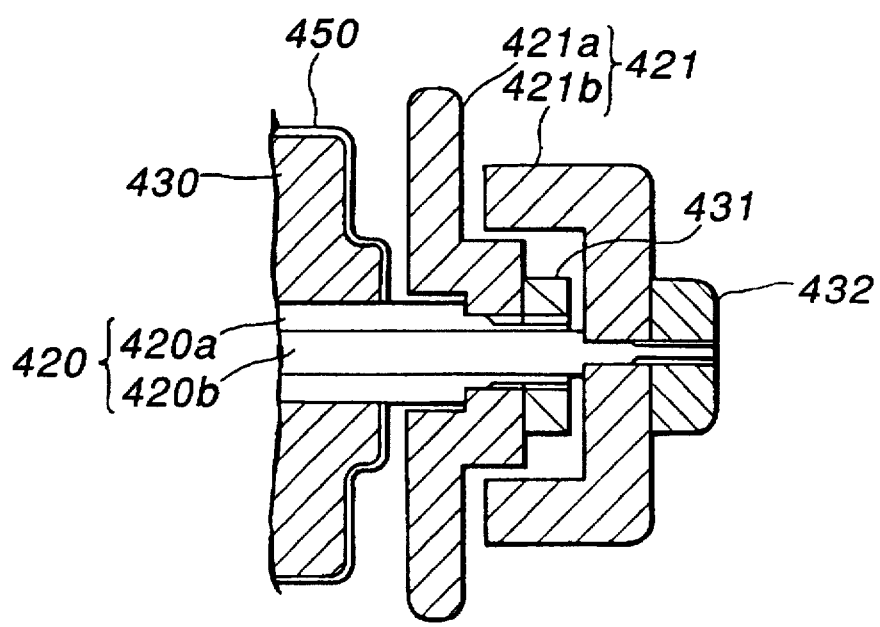

Generally, the cover-type endoscope is covered with the cover followed by fastening the bending control knob to the bending control shaft. The warp control shaft is, as shown in FIG. 2, generally composed of a bending control shaft 420a for the vertical bending operation and a bending control shaft 420b for the lateral bending operation. A control knob 421a for the vertical bending operation is fixed to the bending control shaft 420a by a knob fastening and fixing member 431, while a control knob 421b for the lateral warping operation is fixed to the warp control shaft 420b by a knob fastening and fixing member 432.

In this case, a conventional control-portion cover 450 for covering a control portion 430 of the cover-type endoscope has a hole through which the warp control shaft 420 passes so that the control portion 430 is substantially completely covered with the control-portion cover 450. However, there is a possibility of exposing and contaminating the warp control shaft 420 in the aforesaid state, resulting in a necessity of cleaning and disinfecting the cover-type endoscope.

Therefore, a cover 220 according to this embodiment has an arrangement that a control-portion cover 222 connected to an insertion-portion cover 221 for covering the insertion portion of the cover-type endoscope and arranged to cover the control portion of the cover-type endoscope has a bending control shaft cover member 223 around the hole through which the bending control shaft 230 projecting over the side portion of the control portion, the bending control shaft cover member 223 covering a portion around the bending control shaft 230. As a result, the warp control knob 231 can be fastened in a state where the portion around the bending control shaft 230 is covered with the bending control shaft cover member 223.

That is, this embodiment has an arrangement that the control knob 231a for the vertical warping operation is fixed to the bending control shaft 230a for the vertical bending operation by the knob fastening and fixing member 232 in a state where the portion around the bending control shaft 230 is covered with the bending control shaft cover 223. Then, the control knob 231b for the lateral bending operation is fixed to the bending control shaft 230b for the lateral bending operation by the knob fastening and fixing member 233. As a result, the contamination of the control portion of the cover-type endoscope via the bending control shaft 230 can be prevented, resulting elimination of the necessity of cleaning and disinfecting the endoscope.

Figure 46:
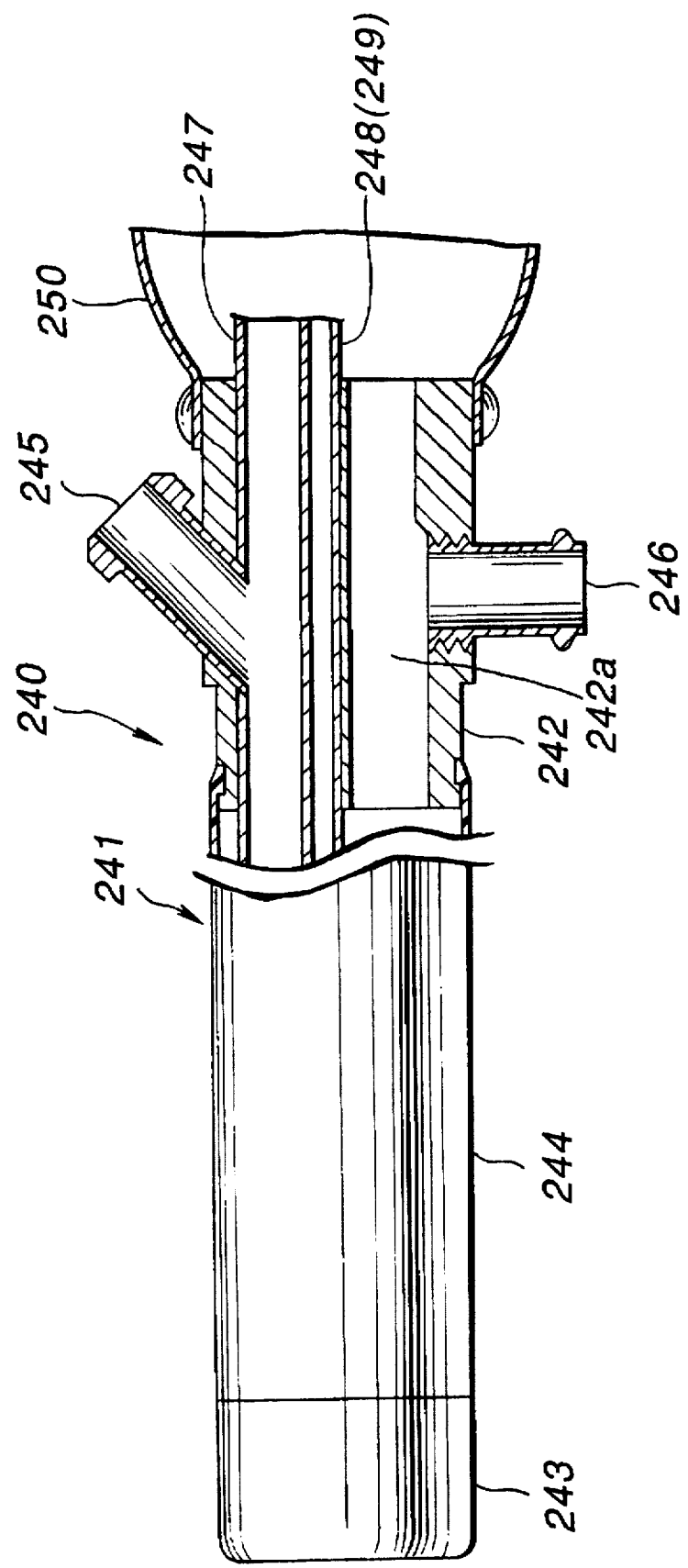
FIGS. 46 and 47 illustrate an eleventh embodiment of the present invention.
Figure 47:
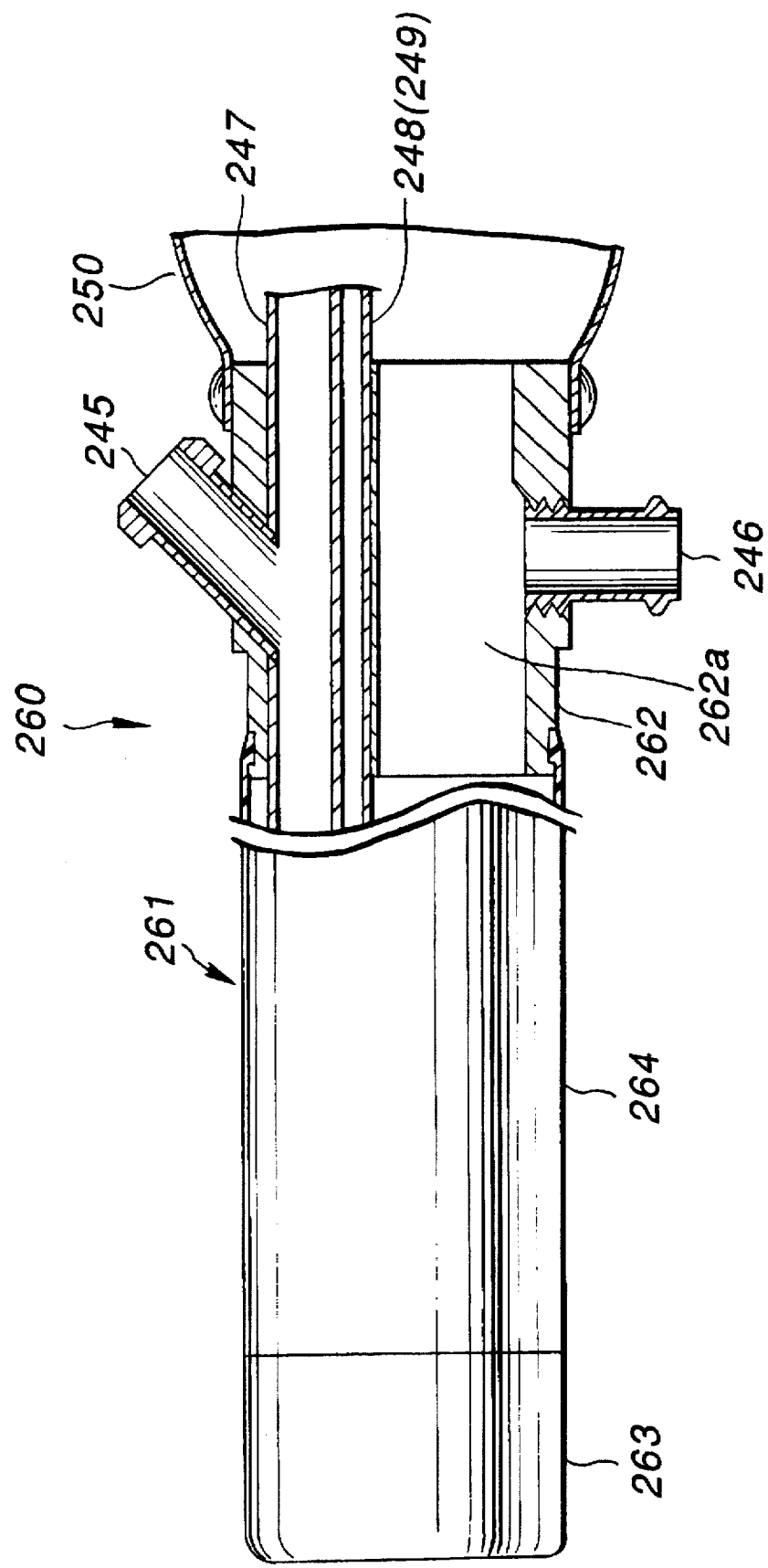

FIGS. 46 and 47 illustrate an eleventh embodiment of the present invention.

Generally, the cover-type endoscopes are classified into cover-type endoscopes each having the bending portion capable of bending in four directions (hereinafter abbreviated to a "four-directional scope") and cover-type endoscopes each having the bending portion capable of bending in two directions (hereinafter abbreviated to a "two-directional scope"). The four-directional scope has the insertion portion, the diameter of which is larger than that of the two-directional scope.

When covers of the same type are similarly used to cover the two-directional scope and the four-direction scope, the endoscope mirror insertion channel to be formed at the joint portion of the cover must have a large size. Therefore, the two-directional scope is fastened to the cover at a joint portion having the endoscope insertion channel, the inner diameter of which is considerably large. It leads to a fact that a difficulty arises at the time of fastening the cover to the cover-type endoscope, resulting in a fear of forming of a pin hole or the like due to the forced operation.

The foregoing problem can be overcome by an arrangement that a cover for the two-directional scope and that for the four-directional scope and each having a proper endoscope insertion channel for fixing the control portion of the scope are individually provided.

That is, a cover 240 for a two-directional scope shown in FIG. 46 has an insertion-portion cover 241 for covering the insertion portion of the cover-type endoscope and a control-portion cover 250 connected to the insertion-portion cover 241 and arranged to cover the control portion of the cover-type endoscope. The insertion-portion cover 241 is composed of a joint portion 242 having an endoscope insertion channel 242a having the inner diameter suitable to fix the control portion of the two-directional scope, a cover leading portion 243, and a flexible insertion-portion cover outer sheath 244 hermetically connected between the joint portion 242 and the cover leading portion 243 and arranged to insulate the insertion portion of the cover-type endoscope from the external environment. The residual structures, such as a forceps insertion port 245, an expansion tube joint 246, a suction tube 247, an air supply tube 248 and a water supply tube 249 are arranged substantially similarly to those according to the foregoing embodiments.

In contrast with the cover 240 for the two-directional scope, a cover 260 for the four-directional scope shown in FIG. 47 comprises an insertion-portion cover 261 including a joint portion 261 having an endoscope insertion channel 261a having the inner diameter suitable to fix the control portion of the four-directional scope and larger than the inner diameter of the endoscope channel 242a. The foregoing arrangement of the joint portion 262 causes the cover leading portion 263 and the insertion-portion cover outer sheath 264 to each have a large diameter. The residual portions are arranged similarly to those of the two-directional scope cover.

As a result, the operation of fastening the cover to each of the two-directional scope and the four-directional scope can simply performed. Furthermore, the joint portions 242 and 262 have different outer diameters to correspond to the inner diameters of the endoscope insertion channels 242a and 262a, resulting in prevention of erroneously fastening of the scope.

By coloring the surface of the joint portions 242 and 262 of the corresponding cover 240 of the two-directional scope and the cover 260 of the four-directional scope into different colors such as pink and blue, the erroneous mounting of the scope can be prevented further assuredly.

Figure 48:
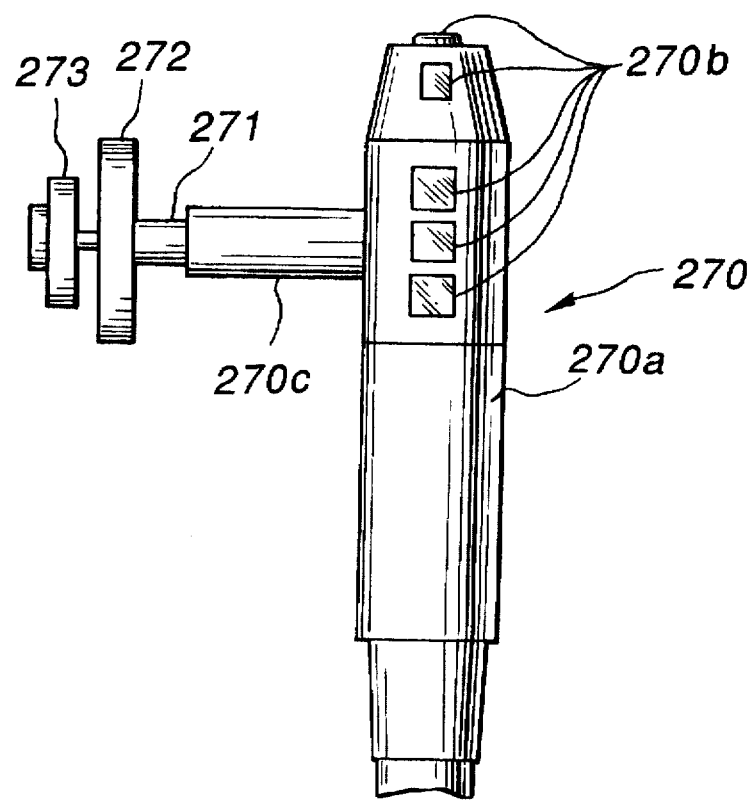
FIGS. 48 and 49 illustrate a twelfth embodiment of the present invention.
Figure 49:
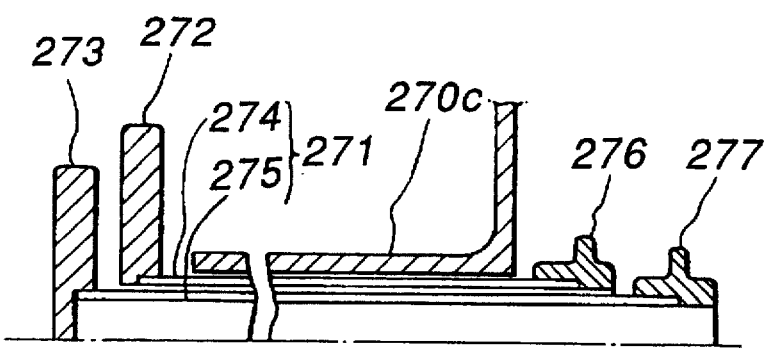

FIGS. 48 and 49 illustrate a twelfth embodiment of the present invention.

Hitherto, the bending control knob disposed in the control portion of the cover-type endoscope is positioned adjacent to the body of the control portion. An operator operates the bending control knob by the hand that holds the insertion portion of the endoscope, resulting in a necessity for the operator to take care not to contaminate the control portion due to a fact that the hand operating the bending control knob touches the body of the control portion.

Accordingly, a control portion 270 of a cover-type endoscope comprising a switch portion 270b in a control portion body 270a has a long bending control shaft 271 that projects over the control portion body 270a also serving as the holding portion. The long bending control shaft 271 is supported by a guide 270c provided in the side portion of the control portion body 270a. As shown in FIG. 49, a bending control shaft 274 for the vertical bending operation has a control knob 272 for the vertical bending operation fastened thereto, while a bending control shaft 275 for the lateral warping operation has a control knob 273 for the lateral warping operation fastened thereto.

The bending control shafts 274 and 275 are connection members for establishing connections between the bending control knobs 272 and 273 and a bending mechanism included in the control portion 62. The bending mechanism in the control portion 270 comprises a chain (omitted from illustration) arranged between sprockets 276 and 277 respectively fastened to the end portions of the warp control shafts 274 and 275. Furthermore, the bending mechanism is connected to the bending block disposed in the bending portion of the endoscope via a wire (omitted from illustration) connected to the foregoing chain. Thus, the rotation of the bending control knob 272 or the warp control knob 273 pushes/draws the wire, causing bending to be realized.

Since the bending control knobs 272 and 273 are positioned sufficiently away from the control portion body 270a as described above, the control portion body 270a is not contaminated even if the contaminated hand operates the bending control knobs 272 and 273.

Figure 50:
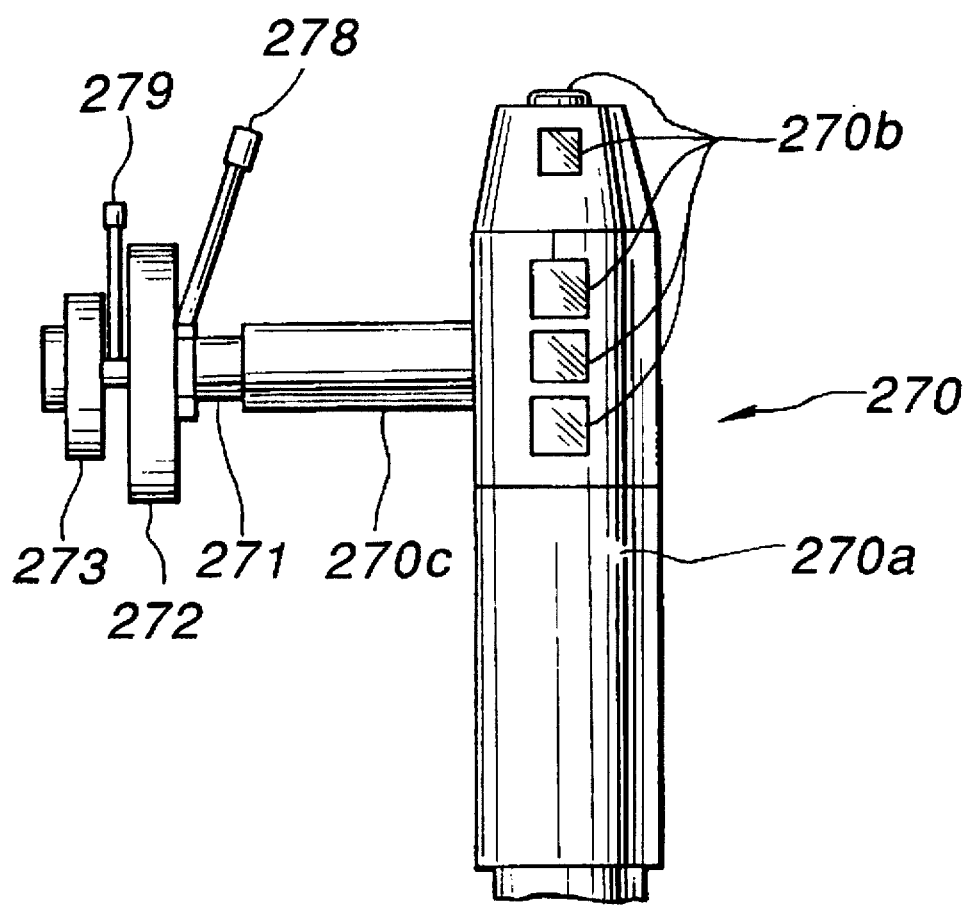
FIG. 50 illustrates a thirteenth embodiment of the present invention.

FIG. 50 illustrates a thirteenth embodiment of the present invention.

In contrast with the twelfth embodiment, this embodiment has an arrangement that engagement knobs 278 and 279 of a bending engagement mechanism for fixing the warp controlling position are, as shown in FIG. 50, positioned sufficiently away from the control portion body 270a similarly to the bending control knobs 272 and 273.

As a result, even if the contaminated hand operates the bending control knobs 272, 273, the warp engagement knobs 278 and 279, the control portion body 270a of the cover-type endoscope is not contaminated similarly to the twelfth embodiment. Therefore, the fear of contamination of the control portion body 270a can be satisfactorily eliminated.

Figure 3:
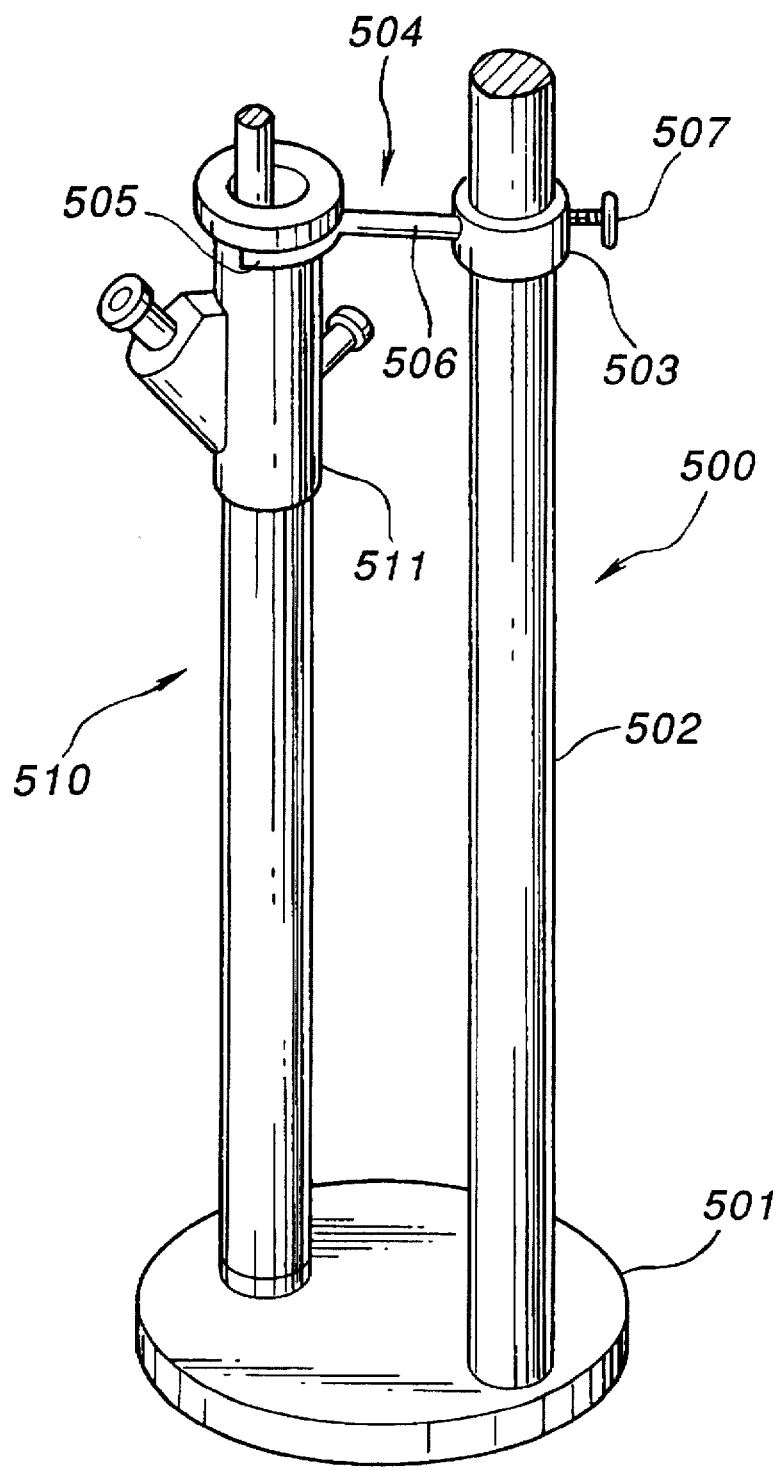
Figure 51:
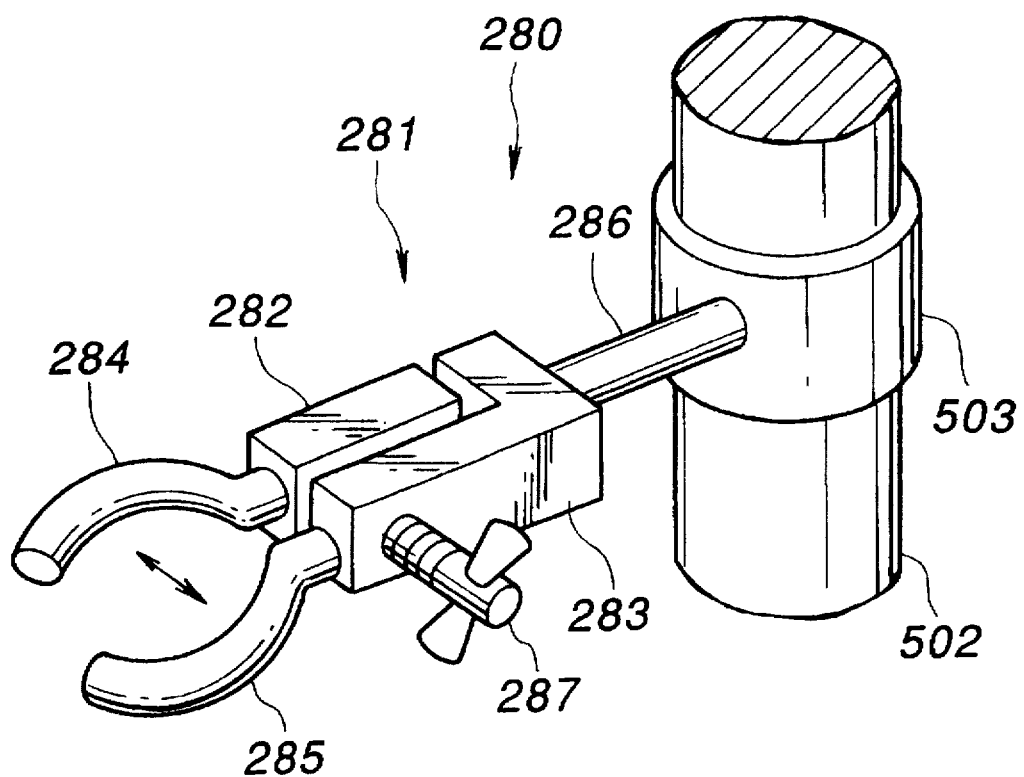
FIG. 51 illustrates a fourteenth embodiment of the present invention.

FIG. 51 illustrates a fourteenth embodiment of the present invention. When the cover is fastened to the cover-type endoscope, the cover is not touched by the hand and is held sanitarily by holding the joint portion of the cover with a cover holder. Hitherto, a cover holder 500, as shown in FIG. 3, has an arrangement that a stand 501 comprising a support member 502 is stood erect, and a cylindrical slidable member 503 to which a holding member 504 for holding a joint portion 551 of a cover 510 vertically slides on the support member 502.

The holding member 504 comprises a fastening member 505 formed into an inverted C-shape and a support rod 506, an end of which is secured to an end portion opposing the opening end of the fastening member 505 and another end of which is secured to the slidable member 503. Thus, the holding member 504 is fastened to a stepped portion in the outer surface of the joint portion 161 to hold the cover. Furthermore, the slidable member 503 has a female thread penetrating in the radial direction thereof, the female thread receiving a fixing screw 507. By loosening the fixing screw 507 to move the slidable member 503 followed by tightening the fixing screw 507, the slidable member 503 can be fixed to an arbitrary position on the support member 502.

Figure 4:
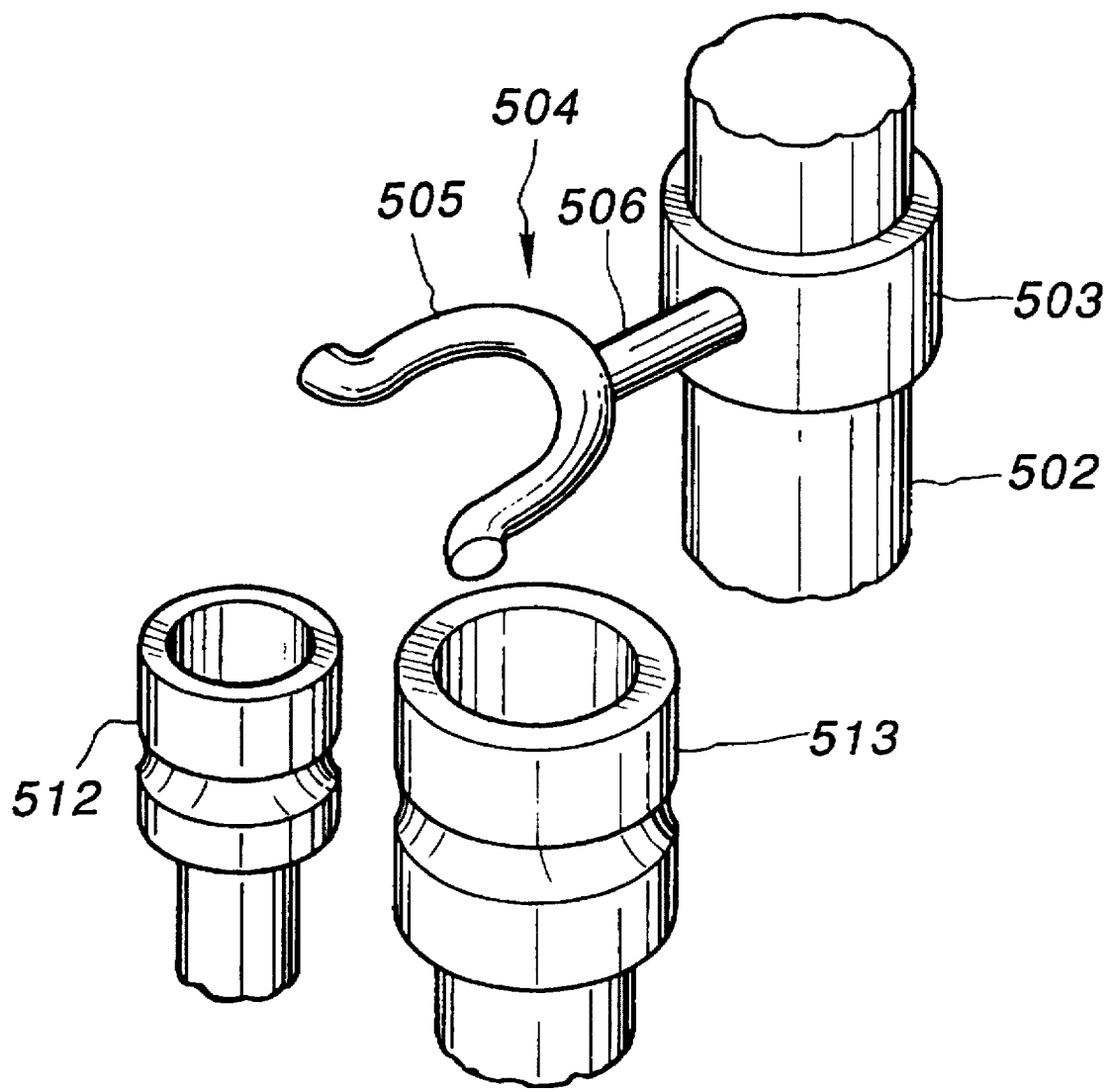

However, the conventional cover holder 500 comprises the holding member 504 capable of holding only a joint portion that has the same diameter as that of the joint portion 511. Therefore, it cannot be adaptable to joint portions having various sizes, for example, it cannot hold joint portions 512 and 513 each having a different diameter from that of the joint portion 511 as shown in FIG. 4.

Accordingly, a cover holder 280 shown in FIG. 51 has an arrangement that is an improvement in the holding member 504 of the conventional cover holder 500 to be adaptable to joint portions having various sizes. The holding member 504 of the conventional cover holder 500 is replaced by a holding member 281 having an arrangement that the holding diameter can be adjusted.

The holding member 281 comprises a pair of blocks 282 and 283, fastening members 284 and 285 each secured to the leading end surface in the lengthwise direction of the blocks 282 and 283, a support rod 286 an end portion of which is secured to the trailing end surface in the lengthwise direction of the block 283 and another end portion of which is secured to the slidable member 503, and an adjustment screw 287 for connecting the two blocks 282 and 283 to each other and adjusting the relative position between the two blocks 282 and 283. The fastening members 284 and 285 form substantially the same shape as that of the foregoing fastening member 505.

By adjusting the relative position between the two blocks 282 and 283 by using the adjustment screw 287, the diameter for holding the joint portion can be changed. Thus, a plurality of joint portions having various sizes can be held.

Figure 52:
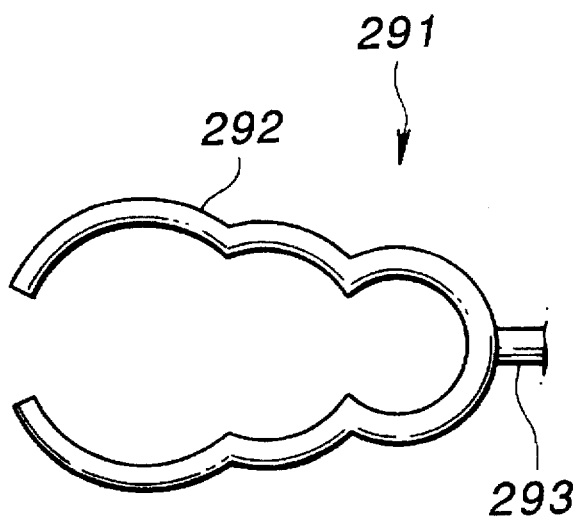
FIGS. 52 to 54 illustrate a fifteenth embodiment of the present invention.
Figure 53:
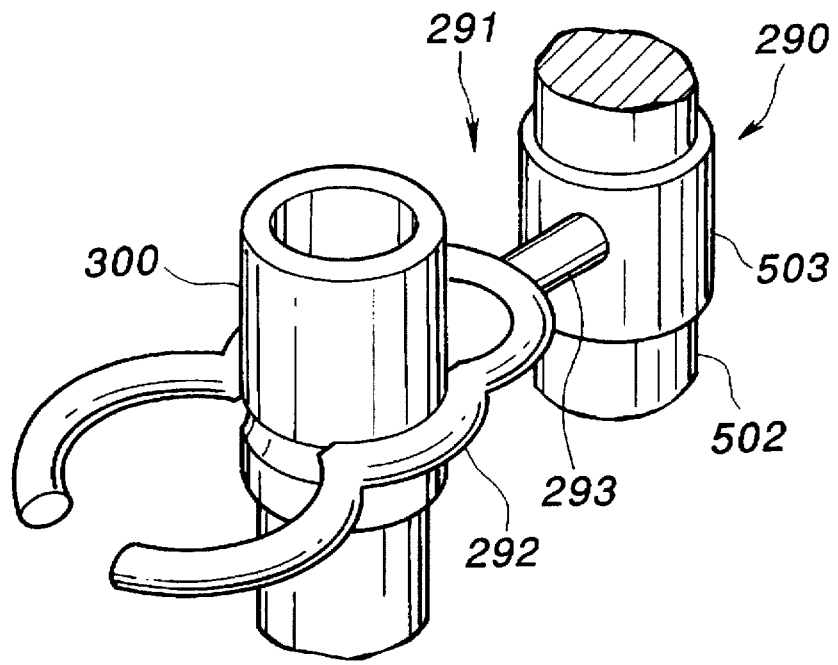
Figure 54:
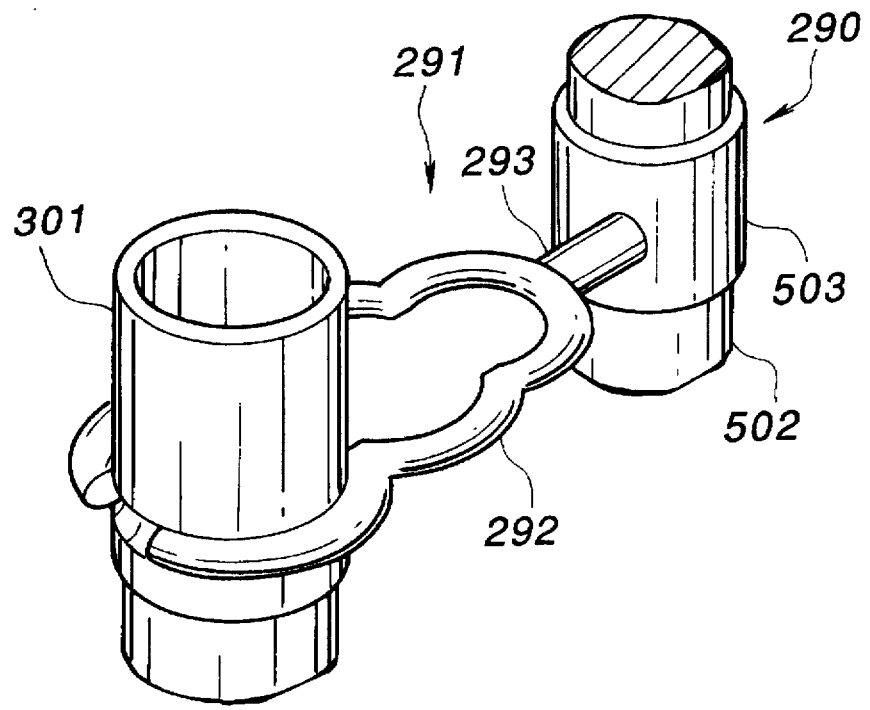

FIGS. 52 to 54 illustrate a fifteenth embodiment of the present invention.

This embodiment has an arrangement that a holding member 291 shown in FIG. 52 is employed in place of the holding member 281 according to the fourteenth embodiment. The holding member 291 having a fastening member 292 formed into a shape realized by connecting a plurality of circular arcs, the diameter of which is enlarged from the base portion toward the leading portion and by opening the leading portion. Furthermore, a support rod 293 to be secured to the slidable member 503 is secured to the base portion.

A cover holder 290 having the holding member 291 is able to hold the joint portion 300 or 301 having different sizes by shifting the holding position as shown in FIGS. 53 and 54. Therefore, a sole cover holder is able to any one of a plurality of covers comprising the joint portions having different sizes.

Although the invention has been described in its preferred form with a certain degree of particularly, it is understood that the present disclosure of the preferred form has been changed in the details of construction and the combination and arrangement of parts may be resorted to without departing from the spirit and the scope of the invention as hereinafter claimed.

What is claimed is:

1. An endoscope apparatus including a cover-type endoscope and an endoscope cover, wherein said cover-type endoscope comprises an insertion portion including a leading portion, a bending portion connected to the leading portion, and a flexible portion connected to the bending portion, wherein said endoscope cover comprises an insertion-portion cover for covering the insertion portion of the cover-type endoscope, said insertion-portion cover including a cover leading portion and an insertion-portion cover outer sheath connected to the cover leading portion, wherein a first portion of the insertion-portion cover outer sheath substantially fits the flexible portion of the insertion portion of the cover-type endoscope when the insertion portion of the cover-type endoscope is positioned within the insertion-portion cover, the first portion of the insertion-portion cover outer sheath having a first degree of uniform flexibility, and wherein a second portion of the insertion-portion cover outer sheath substantially fits the bending portion of the insertion portion of the cover-type endoscope when the insertion portion of the cover-type endoscope is positioned within the insertion-portion cover, the second portion of the insertion-portion cover outer sheath having a second degree of uniform flexibility which differs from the first degree of flexibility.

2. An endoscope apparatus as recited in claim 1, wherein said first degree of uniform flexibility is greater than said second degree of uniform flexibility.

3. An endoscope apparatus including a cover-type endoscope and an endoscope cover, wherein said cover-type endoscope comprises an insertion portion including a leading portion, a bending portion connected to the leading portion, and a flexible portion connected to the bending portion, wherein said endoscope cover comprises an insertion-portion cover for covering the insertion portion of the cover-type endoscope, said insertion-portion cover including a cover leading portion and an insertion-portion cover outer sheath connected to the cover leading portion, the insertion-portion cover further including at least one channel, wherein a first portion of the insertion-portion cover outer sheath substantially fits the flexible portion of the insertion portion of the cover-type endoscope when the insertion portion of the cover-type endoscope is positioned within the insertion-portion cover, the first portion of the insertion-portion cover outer sheath having a first degree of uniform flexibility, wherein a second portion of the insertion-portion cover outer sheath substantially fits the bending portion of the insertion portion of the cover-type endoscope when the insertion portion of the cover-type endoscope is positioned within the insertion-portion cover, the second portion of the insertion-portion cover outer sheath having a second degree of uniform flexibility which differs from the first degree of flexibility.

4. An endoscope apparatus as recited in claim 3, wherein said first degree of uniform flexibility is greater than said second degree of uniform flexibility.

* * * * *